(12) United States Patent
Ayer et al.

(10) Patent No.: US 6,528,620 B1
(45) Date of Patent: Mar. 4, 2003

(54) SID-POLYAMIDE FUSIONS: A POTENT METHOD OF REGULATING GENE EXPRESSION

(75) Inventors: Donald E. Ayer, Salt Lake City, UT (US); Andrew N. Billin, Cary, NC (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/708,906

(22) Filed: Nov. 8, 2000

Related U.S. Application Data

(60) Provisional application No. 60/163,960, filed on Nov. 8, 1999.

(51) Int. Cl.$^7$ .............................. C07K 7/00; C12P 21/02
(52) U.S. Cl. ..................... 530/327; 435/69.1; 435/69.7; 530/333; 530/350
(58) Field of Search ................................ 530/300, 350, 530/333, 327; 435/69.1, 69.7

(56) References Cited

U.S. PATENT DOCUMENTS 5,989,910 A * 11/1999 Mermod et al.

FOREIGN PATENT DOCUMENTS

WO    WO 00/40605    7/2000

OTHER PUBLICATIONS

Amara, Jane F. et al.; A versatile synthetic dimerizer for the regulation of protein–protein interactions; Proc. Natl. Acad. Sci. USA, vol. 94, Sep. 1997; pp. 10618–10623.

Ayer, Donald E. et al.; Mad–Max Transcriptional Repression is Mediated by Ternary Complex Formation with Mammalian Homologs of Yeast Repressor Sin3; Cell, vol. 80, Mar. 10, 1995; pp. 767–776.

Ayer, Donald E. et al.; Mad: A Heterodimeric Partner for Max That Antagonizes Myc Transcriptional Activity; Cell, vol. 72, Jan. 29, 1993; pp. 211–222.

Ayer, Donald E. et al.; Mad Proteins Contain a Dominant Transcription Repression Domain; Molecular and Cellular Biology, vol. 16, No. 10, Oct. 1996; pp. 5772–5781.

Baird, Eldon E., et al.; Solid Phase Synthesis of Polyamides Containing Imidazole and Pyrrole Amino Acids; J. Am. Chem. Soc. , 1996; pp. 6141–6146.

Beerli, Roger R. et al.; Toward controlling gene expression at will: Specific regulation of the erbB–2/HER–2 promoter by using polydactyl zinc finger proteins constructed from modular building blocks; Proc. Natl. Acad. Sci. USA, vol. 95, Dec. 1998; pp. 14628–14633.

Brubaker, Kurt et al.; Solution Structure of the Interacting Domains of the Mad–Sin3 Complex: Implications for Recruitment of a Chromatin–Modifying Complex; Cell, vol. 103, Nov. 10, 2000; pp. 655–665.

Clackson, Tim et al.; Redesigning an FKBP–ligand interface to generate chemical dimerizers with novel specificity; Proc. Natl. Acad. Sci. USA, vol. 95, Sep. 1998; pp. 10437–10442.

Dickinson, Liliane A. et al.; Inhibition of RNA polymerase II transcription in human cells by synthetic DNA–binding ligands; Proc. Natl. Acad. Sci. USA, vol. 95, Oct. 1998; pp. 12890–12895.

Dickinson, Liliane A. et al.; Anti–repression of RNA Polymerase II Transcription by Pyrrole–Imidazole Polyamides; Biochemistry, vol. 58, No. 55, 1999; pp. 10801–10807.

Dickinson, Liliane A., et al.; Inhibition of Ets–1 DNA Binding and Ternary Complex Formation between Ets–1, NF–κB, and DNA by a Designed DNA–binding Ligand; The Journal of Biological Chemistry, vol. 274, No. 18, Apr. 30, 1999; pp. 12765–12773.

Eilers, Alanna L., et al.; A 13–Amino Acid Amphipathic α–Helix Is Required for the Functional Interaction between the Transcriptional Repressor Mad1 and mSin3A; The Journal of Biological Chemistry, Vo. 274, No. 46, Nov. 12, 1999; pp. 32750–32756.

Hassig, Christian A. et al.; Histone Deacetylase Activity Is Required for Full Transcriptional Repression by mSin3A; Cell, vol. 89, May 2, 1997; pp. 341–347.

Ho, Steffan N., et. al.; Dimeric ligands define a role for transcriptional activation domains in reinitiation; Nature, vol. 382, Aug. 29, 1996; pp. 822–826.

Hurlin, Peter J., et al.; Mad3 and Mad4: novel Max–interacting transcriptional repressors that suppress c–myc dependent transformation and are expressed during neural and epidermal differentiation; The EMBO Journal, vol. 14, No. 22, 1995; pp. 5646–5659.

Hurlin, Peter J.; Mnt, a novel Max–interacting protein is coexpressed with Myc in proliferating cells and mediates repression at Myc binding sites; Genes and Development, 1997; pp. 44–58.

Janssen, Sam et al.; Chromatic Opening of DNA Satellites by Targeted Sequence–Specific Drugs; Molecular Cell, vol. 6, Nov. 2000; pp. 999–1011.

Janssen, Sam et al.; Specific Gain–and Loss–of–Function Phenotypes Induced by Satellite–Specific DNA–Binding Drugs Fed to *Drosophila melanogaster*, Molecular Cell, vol. 6, Nov. 2000; pp. 1013–1024.

(List continued on next page.)

*Primary Examiner*—James Ketter
*Assistant Examiner*—Bronwen M. Loeb
(74) *Attorney, Agent, or Firm*—Madson & Metcalf

(57) ABSTRACT

This invention relates to a thirteen amino acid polypeptide sequence which is able to autonomously function as a transcription repression domain through its ability to bind mSin3A. Disclosed herein are compounds and methods for regulating transcription of a selected gene. Compounds include fusions of this repression domain to a DNA-binding domain, such as a polyamide or zinc finger domain. Methods are provided for constructing and for using such compounds to regulate transcription of a selected gene.

26 Claims, 7 Drawing Sheets

OTHER PUBLICATIONS

Kasten, Margaret M.; SIN3–Dependent Transcriptional Repression by Interaction with the Mad1 DNA–Binding Protein; Molecular and Cellular Biology, vol. 16, No. 8, Aug. 1996; pp. 4215–4221.

Koskinen, Päivi J., et al.; Repression of Myc–Ras Cotransformation by Mad Is Mediated by Multiple Protein–Protein Interactions; Cell Growth & Differentiation, vol. 6, Jun. 1995; pp. 623–629.

Laherty, Carol D., et al.; Histone Deacetylases Associated with the mSin3 Corepressor Mediate Mad Transcriptional Repression; Cell, vol. 89, May 2, 1997; pp. 349–356.

Liu, Qiang et al.; Design of polydactyl zinc–finger proteins for unique addressing within complex genomes; Proc. Natl. Acad. Sci. USA, vol. 94, May 1997; pp. 5525–5530.

Lutterbach, Bart, et al.; A Mechanism of Repression by Acute Myeloid Leukemia–1, the Target of Multiple Chromosomal Translocations in Acute Leukemia; The Journal of Biological Chemistry, vol. 275, No. 1, Jan. 7, 2000; pp. 651–656.

Mapp, Anna K., et al.; Activation of gene expression by small molecule transcription factors; PNAS, vol. 97, No. 8, Apr. 11, 2000; pp. 3930–3935.

Parks, Michelle E., et al.; Recognition of 5'–(A,T)GG(A,T)$_2$–3' Sequences in the Minor Groove of DNA by Hairpin Polyamides; J. Am. Chem. Soc., 1996; vol. 118(26) pp. 6153–6159.

Parks, Michelle E., et al.; Optimization of the Hairpin Polyamide Design for Recognition of the Minor Groove of DNA; J. Am. Chem. Soc., 118, 1996; pp. 6147–6149.

Pilch, Daniel S., et al.; Binding of a hairpin polyamide in the minor groove of DNA: Sequence–specific enthalpic discrimination; Proc. Natl. Acad. Sci. USA, vol. 93, Aug. 1996; pp. 8306–8311.

Pruschy, Martin N., et al.; Mechanical studies of a signaling pathway activated by the organi dimerizer FK1012; Chemistry & Biology, 1994; pp. 163–172.

Roussel, Martine F., et al.; Inhibition of Cell Proliferation by the Mad1 Transcriptional Repressor; Molecular and Cellular Biology, vol. 16, No. 6, Jun. 1996; pp. 2796–2801.

Schreiber–Angus, Nicole, et al.; An Amino–Terminal Domain of Mxi1 Mediates Anti–Myc Oncogenic Activity and Interacts with a Homolog of the Yeast Transcriptional Repressor SIN3; Cell, vol. 80, Mar. 10, 1995; pp. 777–786.

Segal, David J., et al.; Toward controlling gene expression at will: Selection and design of zinc finger domains recognizing each of the 5'–GNN–3' DNA target sequences; Proc. Natl. Acad. Sci. USA, vol. 96, Mar. 1999; pp. 2758–2763.

Spencer, David M., et al.; Controlling Signal Transduction with Synthetic Ligands; Science, vol. 262, Nov. 12, 1993; pp. 1019–1024.

Skowyra, Dorota, et al.; Differential Association of Products of Alternative Transcripts of the Candidate Tumor Suppressor ING1 with the mSin3/HDAC1 Transcriptional Corepressor Complex; Manuscript M007664200 JBC Papers in Press, Dec. 15, 2000.

Trauger, John W., et al.; Extended hairpin polyamide motif for sequence–specific recognition in the minor groove of DNA; Chemistry & Biology, May 1996; pp. 369–377.

Trauger, John W., et al.; Recognition of DNA by designed ligands at subnanomolar concentrations; Nature, vol. 382, Aug. 8, 1996; pp. 559–561.

Trauger, John W., et al.; Extension of Sequence–Specific Recognition in the Minor Groove of DNA by Pyrrole–Imidazole Polyamides to 9–13 Base Pairs; J. Am. Chem. Soc., vol. 118, 1996; pp. 6160–6166.

Tutter, Antonin, et al.; Chemicals that footprint DNA: Hitting HIV–1 in the minor groove; Proc. Natl. Acad. Sci. USA, vol. 95, Oct. 1998; pp. 12739–12741.

Wade, Warren S., et al.; Design of Peptides That Bind in the Minor Groove of DNA at 5'–(A,T)G(A,T)C(A,T)–3' Sequences by a Dimeric Side–by–Side Motif; J. Am. Chem. Soc., vol. 114, 1992; pp. 8783–8794.

White, Sarah, et al.; Recognition of the four Watson–Crick base pairs in the DNA minor groove by synthetic ligands; Nature, vol. 391, Jan. 29, 1998; pp. 468–470.

Wang, Huaming et al.; The *Saccharomyces cerevisiae* SIN3 Gene, a Negative Regulator of HO, Contains Four Paired Amphipathic Helix Motifs; Molecular and Cellular Biology, Nov. 1990; pp. 5927–5936.

Yang, Quan, et al.; The winged–helix/forkhead protein myocyte nuclear factor β (MNF–β) forms a co–repressor complex with mammalian Sin3B; Biochem J., vol. 345, 2000; pp. 335–343.

Youn, Hong–Duk, et al.; Cabin1 Represses MEF2–Dependent Nur77 Expression and T Cell Apoptosis by Controlling Association of Histone Deacetylases and Acetylases with MEF2; Immunity, vol. 13, Jul. 2000; pp. 85–94.

Zervos, Antonis S., et al.; Mxi1, a Protein That Specifically Interacts with Max to Bind Myc–Max Recognition Sites; Cell, vol. 72, Jan. 29, 1993; pp. 223–232.

* cited by examiner

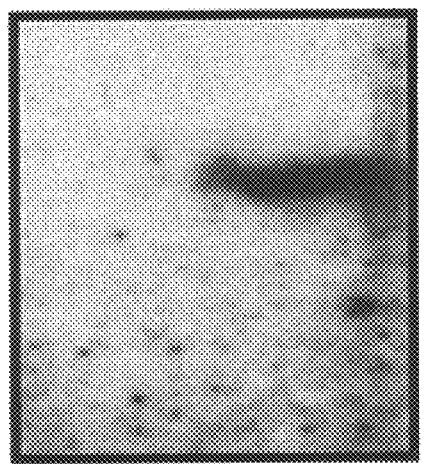
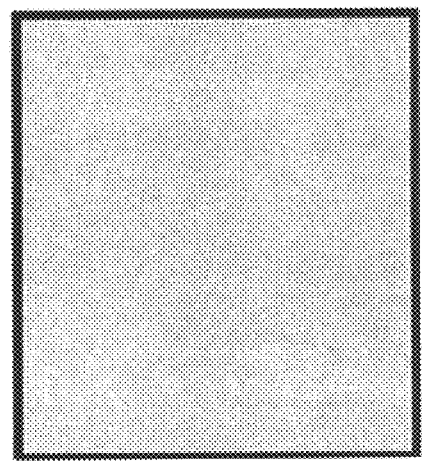
Fig. 1A
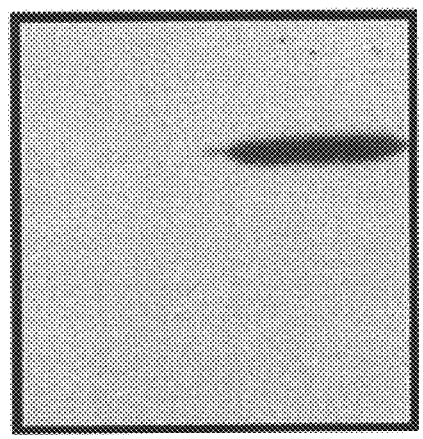
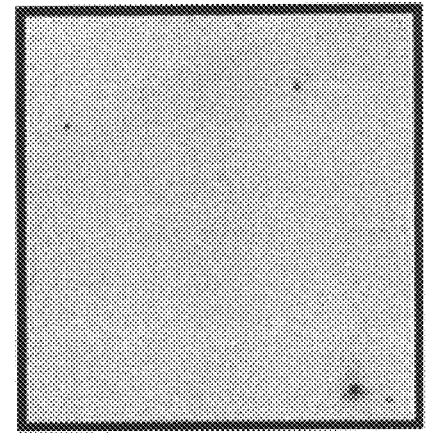
Fig. 1B

```
                         •  •  •  20           27
Mad1(murine)     7   MNIQL LLEAA DYLE......RRERE...A EHGYAS ML P  35
Mad1(human)      7   MNIQM LLEAA DYLE......RRERE...A EHGYAS ML P  35
Mad4(murine)     4  .NSLLL LLEAA EYLE......RRDRE...A EHGYAS ML P  32
Mad4(human)      4  .NSLLI LLEAA EYLE......RRDRE...A EHGYAS VL P  32
Mad3(murine)     6  .SNIQV LLQAA EFLE......RRERE...A EHGYAS LC P  34
Mxi1(human)      7  .INVQR LLEAA EFLE......RRERE...C EHGYAS SF P  35
Mxi1(murine)     7  .INVQR LLEAA EFLE......RRERE...C EHGYAS SF P  35
Mxi1(fish)      23   KNVQV LLEAA SYIE......SAERKDGKC EHGYAS TF P  53
Mnt (human)      2  .MSIET LLEAA RFLEWQAQQQQRARE 25
Mnt (murine)     2  .MSIET LLEAA RFLEWQAQQQQRARE 25
Mad (nematode)   6  . NLGH LLTAA RLLD......IGALD 23.
```

*Fig. 2A*

SID deletion mutants:                              % control β-gal activity

SID 1-57          MAAAVRMNIQMLLEAADYLERREREAE....        100%
SID 1-57          MAAAVRMNIQMPLEAPDYLERREREAE....        0.25%
(L12P/A16P)
SID 1-27          MAAAVRMNIQMLLEAADYLERREREAE            188%
SID 1-27          MAAAVRMNIQMPLEAPDYLERREREAE            0.5%
(L12P/A16P)
SID 7-20                       MNIQMLLEAADYLE          154%
SID 8-20                        NIQMLLEAADYLE           92%
SID 9-20                         IQMLLEAADYLE          6.7%
SID 10-20                         QMLLEAADYLE          0.9%
SID 8-19                        NIQMLLEAADYL           13%
SID 8-18                        NIQMLLEAADY            1.2%

*Fig. 2B*

```
SID point mutants                              % control β-gal activity
                                  8          20
SID 8-20(WT)               NIQMLLEAADYLE           100%
SID 8-20(Q10R)             NIRMLLEAADYLE            25%
SID 8-20(Q10A)             NIAMLLEAADYLE           235%
SID 8-20(E14A)             NIQMLLAAADYLE           215%
SID 8-20(D17A)             NIQMLLEAAAYLE           284%
SID 8-20(Q10A,E14A,D17A)   NIAMLLAAAAYLE           235%
SID 8-20(L13E,A16D)        NIQMELEADDYLE            3.8%
SID 8-20(A15D)             NIQMLLEDADYLE            6.8%
SID 8-20(Y18D)             NIQMLLEAADDLE            5.5%
SID 8-20(L19D)             NIQMLLEAADYDE            4.4%
```

SID-POLYAMIDE FUSIONS: A POTENT METHOD OF REGULATING GENE EXPRESSION

RELATED APPLICATIONS

This application is related to and claims the benefit of United States Provisional Application Serial No. 60/163,960 of Donald E. Ayer and Andrew N. Billin, filed Nov. 8, 1999 and entitled "Sid-Polyamide Fusions: A Potent Method of Regulating Gene Expression," which is incorporated herein by reference.

STATEMENT REGARDING FEDERALLY SPONSORED RESEARCH OR DEVELOPMENT

Work on this invention was sponsored in part by the National Institutes of Health, Grant GM5568-01. The U.S. Government may have certain rights in the invention.

FIELD OF THE INVENTION

The present invention relates to compounds which repress DNA transcription. Specifically, the invention relates to a thirteen amino acid polypeptide sequence which is able to autonomously function as a transcription repressor domain through its ability to independently bind mSin3A. The invention further relates to chimeric transcriptional repressors which comprise the thirteen amino acid polypeptide and a DNA-binding molecule.

TECHNICAL BACKGROUND

Precise changes in gene expression are crucial to both normal and disease processes, Gene expression is regulated by DNA-binding transcription factors and the proteins that interact with these DNA-bound factors. Coactivators and corepressors mediate the ability of DNA-bound transcription factors to modulate gene expression—coactivators by increasing the expression of genes, and corepressors by down-regulating the expression of genes.

Transcriptional regulation depends on the assembly of large multiprotein complexes. For example, the preinitiation complex (Kadonaga, J. T. *Cell* 92: 307–313 (1998)), chromatin remodeling complexes (Cairns, B. R. *Trends Biochem. Sci.* 23:20–25 (1998), Wu, C. *J Biol. Chem.* 272:28171–28174 (1997)), and histone deacetylase-containing corepressor complexes (Rundlett et al., *Proc. Natl. Acad. Sci. USA* 93:14503–14508 (1996), Zhang et al., *Cell* 95:279–289 (1998)) have been shown to be in the $1-2\times10^6$ dalton size range. Molecular connections between proteins in these molecular machines, and the structural basis of their assembly, are not well understood. Initially, transcription repression domains were defined by structure/function analysis, which revealed that, like activation domains, they are more likely to contain particular amino acids rather than have easily identifiable protein-protein interaction domains. This finding led to the hypothesis that activation and repression domains share similar molecular targets and that the structure of the activation or repression domain in itself was not required for function. Transciptional repressors function by at least three distinct mechanisms: by direct contact with components of the basal transcriptional machinery, e.g. even-skipped (Um et al., *Mol. Cell. Biol.* 15:5007–5016 (1995)), Dr1 (Yeung et al., *Genes Dev.* 8424:2097–2109 (1994)), and MOT1 (Auble et al., *Genes Dev.* 8:1920–1934 (1994)); by tethering histone deacetylase-containing corepressor complexes to the promoter, e.g. the Mad family (Hassig et al., *Cell* 89:341–347 (1997), Laherty et al., *Cell* 89:349–356 (1997)), Rb (Brehm et al., *Nature* 391:597–601 (1998), Magnaghi-Jaulin et al., *Nature* 391:601–605 (1998), and Luo et al., *Cell* 92:463–473 (1998)), and MeCP2 (Jones et al., *Nat. Genet.* 19:187–191 (1998), Nan et al., *Nature* 393:386–389 (1998)); or by tethering corepressors that lack deacetylase activity to the promoter, e.g. hairy (Paroush et al., *Cell* 79:805–815 (1994)) and MATα2-MCM1 (Kadosh and Struhl, *Cell* 89:365–371 (1997)). In each of these cases, little or no structural data are available for the repression domain. In contrast, one theme that has emerged recently from the study of activation domains is that relatively short stretches of amino acids can adopt amphipathic α-helical structures and mediate stable functional interactions between transcriptional activators and coactivators. Kussie et al., *Science* 274:948–953 (1996), Radhakrishnan, et al., *Cell* 91:741–752 (1997), and Uesugi et al., *Science* 277:1310–1313 (1997).

Reversible acetylation of the amino-terminal tails of core histones plays an important role in the regulation of gene expression. In general, regions of chromatin that are hyperacetylated are transcriptionally active, while hypoacetylated regions are silenced. Grunstein, M., *Nature* 389–352 (1997). The recent discovery that several transcriptional co-activators are histone acetyltransferases and that co-repressor complexes contain histone deacetylases as active components has provided a mechanistic basis for this correlation. Wolffe and Pruss, *Cell* 84:817–819 (1996), Hassig et al., *Curr. Opin. Chem. Biol.* 1:300–308 (1997), Grant et al., *Trends Cell Biol.* 8:193–197 (1998), Struhl, *Genes Dev.* 12:599–606 (1998), Davie, *Curr. Opin. Genet. Dev.* 8:173–178 (1998). mSin3A and mSin3B were identified as corepressors required for the transcriptional and biological activities of the Mad proteins. Ayer et al., *Cell* 80:767–776 (1995); Schreiber-Angus et al., *Cell* 80:777–786 (1995). mSin3A has recently been shown to be a component of a large multi-protein complex(s) that also contains the histone deacetylases HDAC1 and HDAC2 in apparently stoichiometric amounts. The enzymatic activities of the mSin3A-bound HDACs are required for full transcriptional repression by the Mad family proteins. Hassig et al., *Cell* 89:341–347 (1997); Laherty et al., *Cell* 89:349–356 (1997), Zhang et al., *Cell* 89:357–364 (1997). Subsequently, the mSin3A-HDAC complex has been implicated as a corepressor utilized by a diverse and rapidly expanding collection of transcriptional repressors, including RXR, MeCP2, estrogen receptor, RPX, and Pit1. (Jones et al., *Nat. Genet.* 19:187–191 (1998), Struhl, *Genes Dev.* 12:599–606 (1998), Laherty et al., *Mol. Cell* 2:33–42 (1998), Heinzel et al., *Nature* 387:43–48 (1997), Nagy et al., *Cell* 89:373–380 (1997).

mSin3A and mSin3B and their *Saccharomyces cerevisiae* orthologue SIN3 each contain four similar domains each suggested to form two amphipathic α-helices separated by a flexible linker. Ayer et al., *Cell* 80:767–776 (1995), Wang et al., *Mol. Cell Biol.* 10:5927–5936 (1990). These regions, termed PAH domains for paired amphipathic α-helix, were originally proposed to function as protein-protein interaction domains. Wang et al., *Mol. Cell Biol.* 10:5927–5936 (1990). Recent experiments have demonstrated this to be the case. For example, Mad proteins interact with PAH2 (Ayer et al., *Cell* 80:767–776 (1995), Schreiber-Angus et al., *Cell* 80:777–786 (1995)), a repression domain of the nuclear hormone corepressor N-CoR interacts with PAH1 (Heinzel et al., *Nature* 387:43–48 (1997), Alland et al., *Nature* 387:49–55 (1997)), and the mSin3 interacting protein SAP30 binds to PAH3. (Laherty et al., *Mol. Cell* 2:33–42

(1998). The four PAH domains of the different Sin3 proteins are highly conserved. For example, PAH2 is 90% similar between mSin3A and mSin3B and it is approximately 70% similar to the PAH2 domain of *S. cerevisiae* SIN3 (Ayer et al., *Cell* 80:767–776 (1995)) and recently identified SIN3 homologues from *Schizosaccharomyces pombe, Caenorhabditis elegans, Drosophila melanogaster*, and *Arabidopsis thaliana*. Within a given protein, the four PAH domains are roughly 45% similar with the hydrophobic positions of the putative amphipathic α-helices being most highly conserved, suggesting that PAH domains may share structural features. Ayer et al., *Cell* 80:767–776 (1995); see also Kasten et al., *Mol. Cell. Biol.* 16:4215–4221 (1996) (demonstrating that human Mad1 can interact with yeast SIN3). With the exception of the Mad family, the domains required for Sin3 binding of the other SIN3 interacting proteins, SAP30, SAP18, N-CoR, UME6, HDAC1, and HDAC2, etc., share no obvious sequence similarity.

The Mad family of basic region-helix-loop-helix-leucine zipper (bHLHZip) proteins functions as transcriptional repressors and antagonize the transcriptional and transforming activity of the Myc proto-oncogenes. Ayer et al., *Cell* 72:211–222 (1993), Koskinen et al., *Cell Growth Differ.* 6:623–629 (1995), Lahoz et al., *Proc. Natl. Acad. Sci. USA* 91:5503–5507 (1994), Hurlin et al.,*EMBO J.* 14:5646–5659 (1995), and Vastrik et al., *J. Cell Biol.* 128:1197–1208 (1995). Currently, four Mad family members have been identified: Mad1, Mxi1, Mad3, and Mad4. Ayer et al., *Cell* 72:211–222 (1993), Hurlin et al., *EMBO J.* 14:5646–5659 (1995), Zervos et al., *Cell* 72:223–232 (1993). These proteins share extensive sequence homology throughout their entire open reading frames, with the highest degree of conservation within the bHLHZip and for mSin3 interaction domains (SID). Hurlin et al., *EMBO J.* 14:5646–5659 (1995). The bHLHZip domain is required for dimerization with the bHLHZip protein Max and DNA binding, while the SID is required for interaction with mSIN3A or mSin3B. Schreiber-Angus et al., *Cell* 80:777–786 (1995), Ayer et al., *Cell* 72:211–222 (1993), and Hurlin et al., *EMBO J.* 14:5646–5659 (1995). This SID sequence from Mad1 has been modeled as an amphipathic α-helix. Ayer et al., *Cell* 80:767–776 (1995). Recently, another bHLHZip protein termed Mnt, which shares homology to the Mad family within these two regions, has been identified. Mnt also interacts with Max and can repress transcription in a mSin3-dependent manner and therefore appears to be functionally equivalent to the Mad family proteins. Hurlin et al., *Genes Dev.* 11:44–58 (1997).

Several lines of experimental evidence suggest that interaction between the Mad proteins and Mnt and mSin3A or mSin3B is critical for their function as transcriptional repressors. Mad1 proteins with point mutations in the SID no longer repress transcription, block Myc+Ras cotransformation, or arrest cells in the $G_1$ phase of the cell cycle. Ayer et al., *Cell* 80:767–776 (1995), Koskinen et al., *Cell Growth Differ.* 6:623–629 (1995), Roussel et al., *Mol. Cell Biol.* 16:2796–2801 (1996). Similarly, deletions of amino-terminal regions that contain the SID in Mad3, Mad4, and Mnt severely affect their biological function. Hurlin et al., *EMBO J.* 14:5646–5659 (1995), Hurlin et al., *Genes Dev.* 11:44–58 (1997). Finally, Mxi1 is encoded by two alternatively spliced mRNAs, only one of which encodes a Mxi1 protein with a SID. This protein, Mxi1-SR, is much more potent at blocking Myc+Ras cotransformation than is an Mxi1 isoform which lacks a SID. Schreiber-Angus et al., *Cell* 80:777–786 (1995).

Since current methods for modulating gene expression are laborious and often ineffective, the development of small molecule repressors would constitute a major advance in the art. Additionally, since many human diseases are characterized by the misexpression of a gene, the development of new methods for safely and effectively repressing the transcription of such genes would also be an advance in the art.

From the foregoing, it will be appreciated that it would be an advancement in the art to provide a peptide comprising the minimal SID domain necessary to interact with the PAH2 region of mSin3A/B. It would be a further advancement to provide chimeric transcriptional repressors that could repress the expression of selected genes. It would also be an advancement to provide methods that allow selective repression of gene expression.

Such compounds and methods are disclosed herein.

BRIEF SUMMARY OF THE INVENTION

The present invention relates to a small polypeptide and variants thereof that are capable of interacting with the Sin3 corepressor. These polypeptides are portable repression domains that confer the property of dominant transcriptional repression upon heterologous DNA binding molecules. The polypeptides of the invention permit the synthesis of small molecule regulators of gene expression. Further, since such a polypeptide constitutes a minimal repression domain, it greatly facilitates the production of chimeric transcriptional regulators by conventional gene cloning techniques. The present invention therefore provides chimeric transcriptional repressors comprising such polypeptides and a DNA-binding domain. In certain embodiments, the DNA-binding domain is a polyamide. Preferably, the polyamide is capable of binding a regulatory region of a gene. In certain other embodiments, the DNA-binding domain comprises a zinc finger domain. Preferably, the zinc finger domain is capable of recognizing a regulatory region of a gene.

Other DNA binding domains are known in the art and may be used to construct chimeric transcriptional regulators of the present invention. Known DNA binding domains include BHLH (basic helix-loop-helix), BHLHLZ (basic helix-loop-helix leucine zipper), BZIP (basic zipper), homeodomains, POU domains, and ETS domains. Additionally, a number of proteins that bind DNA (e.g., the p53 protein) are known that do not contain classical DNA binding motifs. One of skill in the art would appreciate that the DNA binding motifs of such proteins could be used to construct chimeric transcriptional regulators of the present invention.

Chimeric transcriptional regulators of the present invention may include one or more than one SID. In certain embodiments, a chimeric transcriptional regulator of the present invention comprises multiple repeated SIDs.

The present invention also provides derivatives of the polypeptide having both higher and lower Sin3 binding affinities than the wild-type. In certain embodiments, these derivatives are at least 77% identical to the amino acid sequence of SEQ ID NO: 1—that is, at least ten out of thirteen residues are identical. In certain other embodiments, the amino acid sequences of these derivatives are at least 85% or at least 92% identical to the amino acid sequence of SEQ ID NO: 1.

In certain embodiments, the SID is less than thirty-five amino acids in length. In certain preferred embodiments, the SID is about twenty or fewer amino acids in length. In other embodiments, the SID is fourteen or fifteen amino acids in length. In certain preferred embodiments, the SID is thirteen amino acids in length.

The present invention also provides methods for creating transcriptional regulators. In certain embodiments, such methods comprise the steps of (1) synthesizing an mSin3A-binding molecule and (2) linking the mSin3A-binding molecule to a heterologous DNA-binding molecule. In certain embodiments, the mSin3A-binding molecule is at least 77%, at least 85%, or at least 92% identical to the amino acid sequence of SEQ ID NO: 1. In certain embodiments, the DNA-binding molecule comprises a polyamide capable of recognizing a regulatory DNA sequence. In certain other embodiments, the DNA-binding molecule comprises a zinc finger domain capable of recognizing a regulatory DNA sequence.

The mSin3A-binding molecule and the DNA-binding molecule may be linked covalently or non-covalently. In certain embodiments, the linkage is covalent and the linking is accomplished using recombinant DNA technology. In certain other embodiments, the linkage is covalent and the linking is accomplished using the standard protection and coupling chemistry used in the art for BOC peptide synthesis.

In certain other embodiments, the mSin3A-binding molecule and the DNA-binding molecule are linked non-covalently and the linkage is accomplished using biotin-streptavidin interactions. In certain other embodiments, conditional dimerization technology is used to achieve a non-covalent linkage. In yet other embodiments, non-covalent linkage is accomplished using FK506 and FKBP interactions. For example, in one embodiment of the present invention, FK506 binding domains are attached to both the mSin3A-binding molecule and to the DNA-binding molecule. These two molecules will remain apart in the absence of a dimerizer. Upon addition of a dimerizer, such as the synthetic ligand FK1012, the two molecules would fuse.

The present invention also comprises methods of using these polypeptides to repress transcription of a selected gene in a cell. In certain embodiments of the present invention, the selected gene comprises at least one regulatory region and the methods comprise the steps of (1) generating a fusion comprising a DNA-binding molecule and a SID, wherein the DNA-binding molecule binds to a target nucleotide sequence within the at least one regulatory region and the SID comprises an amino acid sequence that is at least 77% identical to the amino acid sequence of SEQ ID NO: 1; and (2) introducing the fusion into the cell under conditions such that the DNA-binding molecule binds to a target nucleotide sequence and transcription is repressed. In certain other embodiments, the DNA-binding molecule binds to a sequence within a structural feature of the gene, such as an intron or exon.

The term "repression" refers to a decreased level of transcription when compared to the level of transcription of the same gene in a comparable cell without the fusion. Techniques for conducting such a comparison are well-known in the art. In certain embodiments, the level of repression is 90%—that is, the transcription of the selected gene is decreased by 90% when compared to the transcription of the same gene in a comparable cell into which the fusion has not been introduced. In certain other embodiments, the level of repression is less than 5%, 5%, 10%, 25%, 50%, 75%, 95%, 99%, or greater than 99%.

The present invention also provides methods for creating a functional disruption of a selected gene in a cell, wherein the selected gene comprises at least one regulatory region and the methods comprise the steps of (1) determrining the sequence of the at least one regulatory region of the gene; (2) designing a DNA-binding peptide which binds a sequence within the regulatory region; (3) constructing a nucleic acid molecule comprising nucleotides which code for a chimeric transcriptional repressor, wherein said chimeric transcriptional repressor comprises the DNA-binding molecule and a SID that comprises an amino acid sequence that is at least 77% identical to the amino acid sequence of SEQ ID NO: 1; and (4) inserting the nucleic acid molecule into the genome of the cell. In certain preferred embodiments, the nucleic acid molecule further comprises an inducible promoter.

The present invention further provides methods for correcting a disease characterized by misexpression of a gene. In certain embodiments, the selected gene comprises at least one regulatory region and the methods comprise the steps of (1) determining the sequence of the at least one regulatory region of the gene; (2) designing a DNA-binding peptide which binds a sequence within the regulatory region; (3) constructing a nucleic acid molecule comprising nucleotides which code for a chimeric transcriptional repressor, wherein said chimeric transcriptional repressor comprises the DNA-binding molecule and a SID comprising an amino acid sequence that is at least 77% identical to the amino acid sequence of SEQ ID NO: 1; and (4) inserting the nucleic acid molecule into the genome of the cell.

These and other features of the present invention will become apparent upon reference to the accompanying figures and upon reading the following detailed description and appended claims.

BRIEF DESCRIPTION OF THE FIGURES

A more particular description of the invention briefly described above will be rendered by reference to the appended figures. These figures only provide information concerning typical embodiments of the invention and are not therefore to be considered limiting of its scope.

FIGS. 1A and 1B demonstrate that the interaction between the SID and PAH2 is direct. PVDF blots with immobilized GST and GST-PAH2 were probed with $^{35}$S-labeled IVT Mad1 His (left panel) and Mad1 (L12P/A16P) His (right panel) that had been purified either under native (1A) or denaturing (1B) conditions. The blots were dried and then exposed to detect bound $^{35}$S-labeled proteins. Equivalent amounts of GST and GST-PAH2 were immobilized in each membrane.

FIGS. 2A and 2B demonstrate the determination of the minimal SID. The amino termini of the Mad family members and Mnt were aligned using the GCG pileup algorithm (2A). Regions of highest conservation were boxed. Amino acid positions 10, 14, and 17, numbering relative to Mad 1, of the SID which are somewhat divergent among these proteins are marked with a filled circle. Interactions between the SID and the PAH2 domain were measured by a directed two-hybrid assay (2B). Amino acids 251–404 of mSin3A encoding the PAH2 domain were fused to the VP16 activation domain and the SID and various mutants were fused to the LexA DNA binding domain. The sequences of the different SID amino- or carboxy-terminal deletion mutants are shown along with the relative β-galactosidase activity of each SID in combination with VP16PAH2 in the yeast strain L40. For SID 1–57, only amino acids 1–27 are shown. The β-galactosidase activity of each mutant was normalized to that measured for LexA fused to amino acids 1–57 of Mad1 in combination with VP16PAH2. The sequences shown in FIG. 2A are given in SEQ ID NO: 2 through SEQ ID NO: 12. The sequences listed in FIG. 2B for SID 1–57 and SID 1–27 are given in SEQ ID NO: 13; the sequences listed for SID 1–57 (L12P/A16P) and SID 1–57 (L12P/A16P) are given in SEQ ID NO: 14. The sequence of SID 8–20 is given in SEQ ID NO: 1. The other SIDs shown in FIG. 2B are amino acid sequences contained within SEQ ID NO: 12.

DETAILED DESCRIPTION OF THE INVENTION

Figures 3A, 3B:
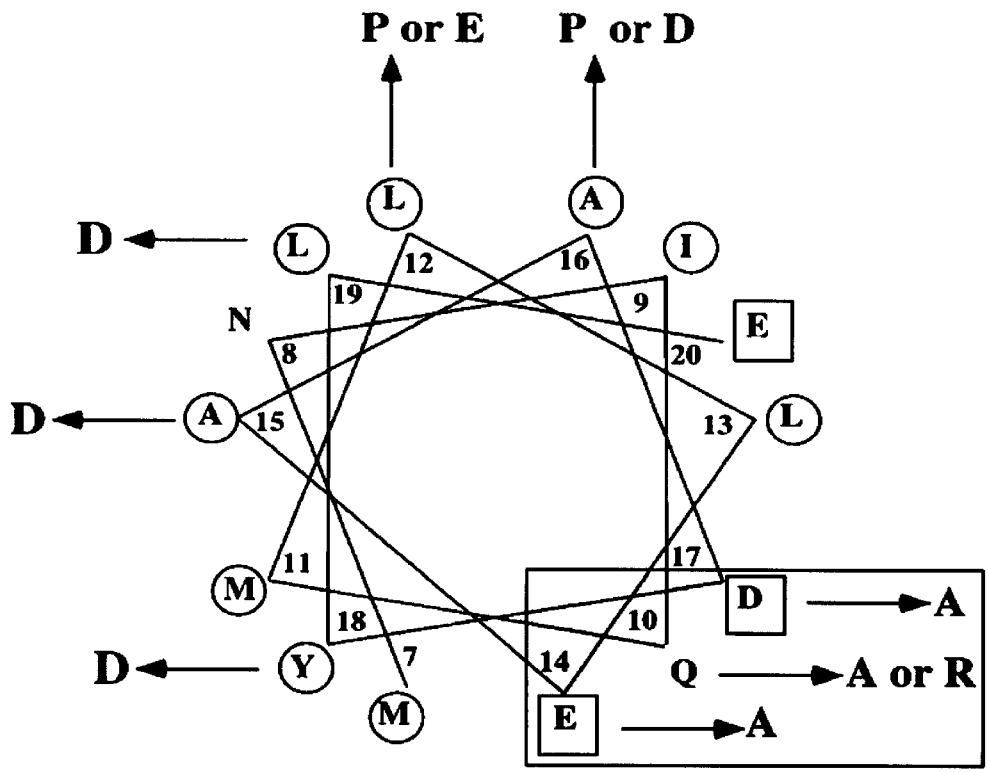
FIGS. 3A and 3B illustrate the determination of residues required for interaction between the SID and PAH2. Amino acids 7–20 of Mad 1 are modeled as an amphipathic α-helix (3A). Hydrophobic and charged residues are circled and boxed, respectively. Amino acids 10, 14, and 17 are potential non-contact residues and are enclosed in a shaded box. The amino acid residues that were mutated are also indicated. The sequences of the different SID mutants are shown along with the relative β-galactosidase activity of each SID in combination with VP16PAH2 in the yeast strain L40 (3B). The β-galactosidase activity of each mutant was normalized to that measured for LexA fused to amino acids 8–20 of wildtype Mad1 in combination with VP16PAH2. The wildtype sequence shown in FIG. 3B is given by SEQ ID NO: 1. The mutant sequences are given in SEQ ID NO: 15 through SEQ ID NO: 23.

The present invention provides a thirteen amino acid polypeptide sequence that is capable of interacting with the eukaryotic corepressor Sin3. In addition, the present invention provides mutant versions of the sequence with both higher and lower affinities for the Sin3 corepressor. These minimal SIDs are useful for creating chimeric transcriptional repressors with different affinities for the Sin3 corepressor. These chimeric transcription factors have both clinical and experimental value, as described below.

The Sin3 is highly conserved throughout eukaryotic evolution and has been identified in all eukaryotic organisms studied thus far. Wang et al., *Mol. Cell Biol.* 10:5927–5936 (1990); Ayer et al., *Cell* 80:767–776 (1995); Schreiber-Agus et al., *Cell* 80:777–786 (1995); Neufeld et al., *Genetics* 148:277–86 (1998). The Mad family of DNA binding transcription factors (Mad1, Mxi, Mad3, Mad4, and Mnt) interact with mSin3A and mSin3B (the mammalian Sin3 proteins) via the Sin3 Interaction Domain ("SID") at the N-terminus of the Mad proteins. Ayer et al., *Cell* 80:767–776 (1995); Schreiber-Agus et al., *Cell* 80:777–786 (1995); Hurlin et al., *EMBO J.* 14:5646–5659 (1995); Ayer et al., *Mol. Cell. Biol.* 16:5772–5781 (1996).

Members of the Mad family of basic region-helix-loop-helix-leucine zipper (bHLHZip) proteins heterodimerize with Max and function to repress the transcriptional and transforming activities of the Myc proto-oncogene. Mad:Max heterodimers repress transcription by recruiting a large multiprotein complex containing the histone deacetylases HDAC1 and HDAC2 to the DNA molecule. The interaction between the Mad proteins and the complex is mediated by the corepressor mSin3A and requires sequences at the amino terminus of the Mad proteins, termed the SID, for Sin3 interaction domain, and the second of four paired amphipathic α-helices (PAH2) in mSin3A. Wang et al., *Mol. Cell Biol.* 10:5927–5936 (1990); Ayer et al., *Cell* 80:767–776 (1995); Schreiber-Agus et al., *Cell* 80:777–786 (1995); Ayer et al., *Mol. Cell. Biol.* 16:5772–5781 (1996); Kasten et al., *Mol. Cell. Biol.* 16:4215–4221 (1996).

Previous work delineated a 30–40 amino acid region of Mad1 and Mxi that could act as a portable repression domain when fused to heterologous DNA binding domains. Ayer et al., *Cell* 80:767–776 (1995); Schreiber-Agus et al., *Cell* 80:777–786 (1995); Hurlin et al., *EMBO J* 14:5646–5659 (1995); Ayer et al., *Mol. Cell. Biol.* 16:5772–5781 (1996); Hurlin et al., *Genes and Dev.* 44–58 (1997). In order for this domain to be useful for the production of small molecule transcriptional repressors, it was necessary to identify the minimal amount of polypeptide needed to act as a portable repression domain. It was not known, however, if smaller peptides—that is, less than about 30–40 amino acids—could also act as portable repression domains.

To understand the structural basis for the direct interaction between the transcriptional repressor Mad1 and its corepressors mSin3A and mSin3B, we defined the minimal sequence of Mad1 required for interaction with PAH2, showed that this minimal interaction domain can adopt an amphipathic α-helical structure in solution and determined that the hydrophobic face of this helix makes key contacts with mSin3A. We had previously shown that the amino-terminal 35 residues of Mad1 functions as a portable repression domain and is required to target functional mSin3A-HDAC complexes. Ayer et al., *Mol. Cell. Biol.* 16:5772–5781 (1996). Here we show that residues 8–20 of Mad1 constitute a minimal functional portable repression domain. Further, our experiments showed that residues 10, 14, and 17 are not required for interaction with PAH2 and that the surface created by these residues does not make important contact with other components of the mSin3A-HDAC complex.

We have used two classes of mutations to determine the structural requirements for the interaction between the SID and PAH2. The first class (L12P/A16P SID and L12E/A16D SID) cannot adopt an α-helical structure and fails to interact with PAH2, suggesting a requirement for this structure in binding to PAH2. The second class of mutations (A15E and L19D) retains helical structure in TFE but fails to interact with PAH2. These mutations are in the hydrophobic face of the SID amphipathic α-helix demonstrating that the hydrophobic face of the SID makes key contacts required for high-affinity interaction with PAH2. We propose that the α-helix correctly positions the hydrophobic residues of the SID and optimizes the hydrophobic interactions required for the SID to bind PAH2.

Without being bound by any particular theory, it appears that the helical nature of the fourteen amino acid SID peptide observed in our CD experiments is likely to reflect its structure in the context of a full-length Mad1. The double proline mutant SID peptide is incapable of α-helix formation even at high concentrations of TFE. The same proline substituted SID in the context of full-length Mad1 disables both the transcriptional repressor and the biological functions of Mad1. Furthermore, the SID has been fused to the DNA binding domain of GAL4, LEXA, and c-Myc and in these contexts can impart transcriptional repression functions to each of these proteins. Ayer et al., *Cell* 80:767–776 (1995), Koskinen et al., *Cell Growth Differ.* 6:623–629 (1995), Roussel et al., *Mol. Cell. Biol.* 16:2796–2801 (1996), Ayer et al., *Mol. Cell. Biol.* 16:5772–5781 (1996), Kasten et al., *Mol. Cell Biol.* b16:4215–4221 (1996). In each of these cases, proline substitution of positions 12 and 16 of the SID result in the loss of repression function of the fusion proteins. Therefore, there is a strict correlation between the inability of the L12P/A16P SID peptide to adopt a helical conformation in TFE and the inability of the SID to function as an autonomous transcription repression domain. The simplest interpretation of these results is that the proline-substituted SID, in the context of the different fusion proteins or full-length Mad1, cannot adopt the helical conformation that is required for a functional interaction between the SID and the mSin3A-HDAC corepressor complex.

The dependence of the interaction between the repression domain of Mad1 and mSin3A on an amphipathic helical structure is reminiscent of the interaction between several activation domains and their target proteins. The p53 activation domain and the KID domain of CREB bury the hydrophobic faces of their helical activation domains into hydrophobic pockets in MDM2 and the KIX domain of CBP, respectively. Kussie et al., *Science* 274:948–953 (1996), Radhakrishnan et al., *Cell* 91:741–752 (1997). Also, the acidic activation domain of VP16 forms an amphipathic α-helix when it contact hTAF$_{II}$31. Uesugi et al., *Science* 277:1310–1313 (1997). In each of these cases, mutation of hydrophobic residues around the binding interface inhibits both interaction and transcriptional activation. Uesugi et al., *Science* 277:1310–1313 (1997), Parker et al., *Mol. Cell* 2:353–359 (1998), Lin et al., *Genes Dev.* 8:1235–1246 (1994). These findings have led to the conclusion that the charged residues in these activation domains are generally unimportant for stable interaction and that interaction is primarily driven by Van der Waals contacts. Our mutagenesis studies on the SID suggest that similar rules will govern the interaction between transcription repressors and their co-repressors.

Another important feature emerging from structural studies on activation domains is that they tend to be unstructured in the absence of their target and adopt their helical structure upon binding. Radhakrishnan et al., *Cell* 91:741–752 (1997), Uesugi et al., *Science* 277:1310–1313 (1997), Hua et al., *Biochemistry* 37:5858–5866 (1998). Each of our mutant SIDs containing alanine substitutions at non-contact residues interact with PAH2 approximately 2-fold better than the wild-type. Because substitutions to alanine at these positions may promote helicity, we speculate that the SID may be unstructured in the absence of PAH2 and that alanine substitution at noncontact residues lowers the activation energy required for the SID to undergo the transition from random coil to helix.

It was not clear what structural features of PAH2 would be required for interaction with the SID. The PAH domains were originally suggested to consist of two amphipathic helices, helix A and B, separated by a flexible linker. Wang et al., *Mol. Cell Biol.* 10:5927–5936 (1990). Proline insertions into helix A of PAH2 and deletion of either the helix A or B of PAH2 eliminate binding to Mad1 or Mxi1, demonstrating the importance of these putative structures for interaction. Schreiber-Angus et al., *Cell* 80:777–786 (1995), Ayer et al., Mol. Cell Biol. 16:5772–5781 (1996). It may be that the PAH2 domain is most structurally similar to the KIX domain of CBP. The KIX domain consists of three α-helices, α1, α2 and α3. α1 and α3 pack approximately parallel to one another and are linked by α2, defining the hydrophobic groove that receives the hydrophobic face of the CREB KID α-helix. Radhakrishnan et al., *Cell* 91:741–752 (1997). Because the linker between the helix A and helix B of PAH2 can be modeled as an α-helix (data not shown), it is possible that helix A and B form a hydrophobic cleft, analogous to that found in the KIX domain, which would receive the hydrophobic face of the SID.

The minimal SID contains thirteen amino acids and is rich in hydrophobic amino acids. One mutant SID, Q10A/E14A/D17A, had hydrophobic amino acids at ten of its thirteen positions and binds two-fold better than wild-type. Therefore, the SID may be characterized as a hydrophobic region of amino acids. However, given that regions of hydrophobic amino acids are relatively common in proteins, it seems unlikely that other mSin3A/B interacting proteins will be identified through simple searches of protein data bases. Several other proteins have been identified that interact with the PAH domains of mSin3A and/or B. The 91 carboxyl-terminal residues of SAP30 interact with PAH3. Laherty et al., *Mol. Cell* 2:33–42 (1998). Two regions of N-CoR interact with mSin3A: residues 1–312 interact with PAH3, and residues 1829–1940 interact with PAH1. Heinzel et al., *Nature* 387:43–48 (1997), Nagy et al., *Cell* 89:373–380 (1997), Wang et al., *Mol. Cell Biol.* 10:5927–5936 (19900, and Alland et al., *Nature* 387:49–55 (1997). SAP30 and the amino-terminal portion of N-CoR lack regions with obvious sequence similarity to the Mad1 SID; however, deletion of an alanine-rich putative α-helix between amino acids 1833 and 1845 of N-CoR interrupts interaction with PAH1. Alland et al., *Nature* 387:49–55 (1997). These findings suggest that protein domains that interact with PAH1 and PAH2 may be similar structurally and distinct from those that interact with PAH3. Current evidence shows that the interaction between Sin3-binding proteins and PAH domains is highly specific. For example, no interaction is detected between Mad1 and PAH1, PAH3 or PAH4 domains of mSin3A using GST pull-down experiments or directed two-hybrid experiments. Ayer et al., *Cell* 80:767–776 (1995). Therefore, while the PAH domains may be structurally related, each must have different requirements for specific protein-protein interaction.

The fifteen amino acid region following the SID, residues 20–35, is highly conserved but it is only found in the vertebrate Mad family proteins. This conserved region is apparently not required for interaction with PAH2, and may have a destabilizing effect of the SID PAH2 interaction. Further, the minimal thirteen amino acid SID functions similarly to the longer 35-amino acid SID in transcription repression experiments, suggesting that residues 20–35 are relatively unimportant for transcription repression. It is possible that this conserved domain plays an ancillary role in binding to PAH2 and repression, but this function is not revealed by the assays employed here. Because the Mad family and Mnt have overlapping, if not identical, DNA binding specificities (Ayer et al., *Cell* 72:211–222 (1993), Hurlin et al., *EMBO J.* 14:5646–5659 (1995), Zervos et al., *Cell* 72:223–232 (1993), Hurlin et al., *Genes Dev.* 11:44–58 (1997)), it is possible that the residues 20–35 may themselves function as a protein-protein interaction domain that will distinguish activity of the Mad family from Mnt or other transcription repressor families that depend on SID-like domains for function.

The present invention provides methods for creating chimeric transcriptional regulators which can be designed to control the expression of any eukaryotic gene. At least two different DNA binding technologies may be used for the production of designed DNA binding modules linked to the minimal SID. The invention produces a molecule with novel properties that make it suitable for regulating eukaryotic gene expression.

The first DNA binding technology involves linking the thirteen amino acid SID to a zinc finger domain designed to bind a desired sequence. The second DNA binding technology involves the fusion of the minimal SID to polyamide molecules. Polyamides can be designed to bind any DNA sequence. The present invention provides methods for the production of a polyamide fused to the thirteen amino acid SID domain (via conventional peptide synthesis techniques). Molecules of this type may be used for both clinical and experimental applications. Such chimeric SID transcriptional repressors offer a major advance in the field of functional genomics as analytical tools to modulate the transcription of any gene being studied in either cell or tissue cultures, or in whole living organisms.

These chimeric repressors are also likely to prove valuable in gene therapy applications. For instance, fusions of the SID to any DNA binding domain could be introduced into a tissue of choice by infection with a virus encoding the fusion or by other DNA transfer techniques. Such fusions may be like those described in the Techniques section which follows (wherein the SID is fused to a designed zinc finger domain or to a polyamide), or to any other DNA binding domain of choice. A gene whose over-expression is causative in disease can be down-regulated in this manner in order to alleviate disease symptoms.

These polyamide-SID fusions provide a small molecule that can be designed to inhibit the expression of any gene desired and thus are a major break-through in drug design. Polyamides are cell permeable, thus making these molecules suitable for use as traditional systemic medications. In addition, because the polyamide can be designed to bind any DNA sequence, only limited knowledge of a target gene's structure is required. This represents a significant advance over current polyamide gene inhibition. The previously-described technology depends on the ability of a polyamide to compete for DNA binding with an endogenous transcription factor. Thus, extensive knowledge of the transcription factor binding sites in the regulatory region of a gene is needed to design an effective polymaide transcription inhibitor. With SID-polyamide fusions, it is not necessary to compete for binding with an endogenous transcription factor. Thus, only limited knowledge of the structure of a gene's regulatory region is needed in order to make an effective SID-polyamide fusion. Also, transcriptional inhibition by the SID-polyamide is active because a corepressor is targeted to the gene of interest. Since the Sin3 corepressor prevents transcription by acting on the chromatin by histone deacetylation, the repressed state of the gene will be stable and not require the continuous presence of the drug.

In describing the present invention, the following terms will be employed, and are intended to be defined as indicated below.

The term "SID" refers to a Sin3 Interaction Domain—a sequence at the amino terminus of the Mad family of proteins discovered to comprise a thirteen amino-acid sequence which forms an amphipathic α-helix with a hydrophobic face in solution. The SID interacts with the second of four paired amphipathic α-helices (PAH2) in mSin3A. Mutagenesis and structural studies of the SID show that amino acids 8–20 of Mad1 are sufficient to mediate the SID:PAH2 interaction. Residues located on the hydrophobic face of the SID helix are required for interaction with PAH2. The SID functions to target the mSin3A/HDAC corepressor complex, and is thus an autonomous and portable repression domain.

The term "PAH2" refers to the second of four paired aniphipathic helices in mSin3A which interacts with the SID of the Mad family proteins through its hydrophobic face.

The term "fusion" refers to a heterologous or chimeric construct comprising a SID or one of its variants bound to a DNA-binding molecule. The bond may be temporary or permanent, inducible or non-inducible, and the DNA-binding molecule may be chosen from natural or synthetic DNA-binding molecules.

The term "misexpression" refers to over- or underexpression of a gene. The term may also refer, e.g., to expression in a tissue in which the gene is ordinarily quiescent or to lack of expression in a tissue in which the gene is usually expressed. "Misexpression" also applies to over- or under-expression of genes at various timepoints in development. The phrase implies a comparison under equivalent conditions in equivalent cells or tissues. Techniques for conducting such a comparison are well known in the art, and include RNA analytical methods, e.g., Northern blotting, and protein analytical methods, e.g., Western blotting.

The terms "regulatory region" and "regulatory DNA sequence" include promoter, enhancer, and transcriptional start sequences, as well as other sequences that affect the level of expression of a particular gene within a cell.

The phrase "conditional dimerization technology" refers to systems for chemically controlled dimerization. Such systems are known in the art. For example, an FK506 binding protein (FKBP) may be linked to each of two molecules whose interaction is to be controlled. In the absence of a dimerizer, the two molecules remain apart. The addition of a dimerizer, such as the synthetic ligand FK1012, causes the two molecules to dimerize. Spencer et al., *Science* 262:1019–1024 (1993); Ho et al., *Nature* 382:822–826 (1996); Pruschy et al., *Chem. Biol.* 1:163–172 (1994); Amara et al., *Proc. Natl. Acad. Sci. USA* 94:10618–10623 (1997); Clackson et al., *Proc. Natl. Acad. Sci. USA* 95:10437–10442 (1998). Different drug binding domains and different chemical dimerizers allow for "mix and match" specificity.

The term "heterologous" denotes sequences that are not normally joined together, and/or are not normally associated with a particular cell. Thus, a "heterologous" region of a recombinant protein is a segment of one protein molecule within or attached to a portion of another protein molecule that is not found in association with the other protein molecule in nature.

The terms "functional disruption" and "knockout" refer to situations in which a particular gene has been targeted and transcriptionally repressed, causing an inability to express the given gene, and thus its product. Using the compounds and methods of the instant invention, such disruptions could be caused fully or partially at any time during the development of a cell or organism, thus allowing study of the effect a given gene has upon development in a given stage.

All references, publications, patents, patent applications, and commercial materials cited in this application are hereby incorporated by reference in their entirety.

Techniques

Techniques have been described for the production and selection of polydactyl zinc-finger proteins that are capable of binding specifically to any DNA sequence. Liu et Ad al., *Proc. Natl. Acad. Sci.* USA 94:5525–5530 (1997); Beerli et al., *Proc. Natl. Acad. Sci.* USA 95:14628–14633 (1998); Segal et al., *Proc. Natl. Acad. Sci. USA* 96:2758–63 (1999). Once the desired zinc finger has been selected, conventional molecular biology techniques can be used to create a chimeric gene that encodes the wild-type or mutant SID desired and the zinc finger of choice. The SID can be placed at either the amino- or carboxy-terminus of the chimeric molecule. The synthetic gene can be expressed from any number of conventional vectors for the expression of the chimeric transcriptional repressor in mammalian cells, insect cells, fungal cells, transgenic animals, transgenic plants, and transgenic fungi. This use of the thirteen amino acid SID is also generally applicable to other DNA binding domains.

The SID can also be fused to synthetic organic molecules, such as polyamides, that have the ability to bind specific sequences of DNA to create novel transcriptional repressors. As an example of the synthesis of such a polyamide-SID fusion we present the synthesis of a fusion that binds to the DNA sequence 5' AGCTGCA 3' (Dickinson et al., *J. Biol. Chem.* 274:12765–12773 (1999)) and a method for using it to repress transcription both in vitro and in cultured cells. This particular polyamide is known to be absorbed by cells in culture and to be biologically active. Dickinson et al., *J. Biol. Chem.* 274:12765–12773 (1999). The synthesis of polyamides can be carried out on an automated peptide synthesizer (ABI 430A) and uses the same protection and coupling chemistry as BOC peptide synthesis. Mapp et al., *Proc. Natl. Acad. Sci. USA* 97:3930–3935 (2000); Baird and Dervan, *Journal of the American Chemical Society* 118:6141–6146 (1996); Parks et al., *Journal of the American Chemical Society* 118:6147–6152 (1996); Pilch et al., *Proc. Natl. Acad. Sci.* USA 93:8306–8311 (1996); Trauger et al., *Chem. Biol.* 3:369–377 (1996); Trauger et al., *Journal of the American Chemical Society* 118:6106–6166 (1996). Synthesis of the polyamide/SID fusion would be initiated as in Baird and Dervan (Baird and Dervan, *Journal of the American Chemical Society* 118:6141–6146 (1996)); however, instead of terminating the synthesis of the polyamide by cleavage from the resin and deprotection, synthesis would continue using standard BOC amino acid synthesis to make the thirteen amino acid SID. Since synthesis of polyamides or peptides in vitro occurs in the opposite direction from naturally occurring protein synthesis, the first added amino acid of the SID would be "E" and the last added amino acid would "N". The completed molecule would be cleaved and deprotected using typical conditions for BOC peptide synthesis. Thus the completed SID-polyamide fusion would have the sequence: NIQMLLEAADYLE-ImPy-$\beta$-ImPy-$\gamma$-ImPy-$\beta$-Impy-$\beta$-Dp, where "NIQMLLEAADYLE" represents the 13 amino acid SID in standard one letter amino acid code (SEQ ID NO: 1), and the polyamide is represented by Im (imidazole), Py (pyrrole), $\beta$ ($\beta$-alanine), $\gamma$ ($\gamma$-aminobutyric acid), and Dp (dimethylaminopropylamide). The SID could also be incorporated at the opposite end of the polyamide by initiating synthesis with the polypeptide and then finishing the synthesis with the polyamide, resulting in the molecule ImPy-$\beta$-ImPy-$\gamma$-ImPy-$\beta$-ImPy-$\beta$-NIQMLLEAADYLE. Any of the mutant SID sequences could be used to produce SID-polyamide fusions with different abilities to bind to Sin3 corepressors.

Other strategies could be used to couple the polyamide to the SID. For instance, a biotinylated polyamide could be made by introducing a biotin-labeled amino acid at the first or last synthetic step. The SID could be synthesized separately with a reactive cysteine at either end of the polypeptide. This residue could be used to attach a strepavidin molecule. Simply mixing the biotin-polyamide and the strepavidin-SID would result in the non-covalent liking of the SID to the polyamide. Alternately, the SID could be genetically engineered as a fusion protein with strepavidin.

The SID-polyamide fusion can be used to repress transcription of a reporter gene linked to a minimal promoter and 4 or 5 reiterated 5' AGCTGCA 3' sites (the cognate binding site for the polyamide described above) in animal cells. Alternately, it could be used in an in vitro transcription reaction with a similar reporter.

In the context of gene therapy applications, wherein a chimeric transcriptional repressor could be used to regulate the expression of a gene whose expression drives a disease phenotype, many methods of gene transfer are available, including the use of recombinant viruses such as retroviruses, herpesviruses, pox viruses, and adeno-associated viruses; as well as non-viral methods such as transfection, liposome-mediated transfer, and electroporation.

Recombinant retroviruses are frequently used for gene transfer, and methods for constructing such viruses are known in the art. Hodgson, *Bio/Technology* 13:222–225 (1995); see, e.g., Miyanohara et al., *Proc. Natl. Acad. Sci. USA* 85:6538–6542 (1988); Rosenberg et al., *New England J. Med.* 323:570–578 (1990).

Methods for producing recombinant adeno-associated viruses (rAAV) are also known in the art. Briefly, a suitable producer cell line is transfected with an AAV vector containing the gene of interest. AAV helper functions (i.e., the products of the AAV rep and cap genes) and accessory functions, which are typically derived from a helper virus such as adenovirus or herpesvirus, are then expressed in the producer cell. Once these factors come together, the gene of interest is replicated and packaged as though it were a wild-type AAV genome, forming a recombinant virion. When a patient's cells are infected with the resulting rAAV virions, the gene of interest enters and is expressed in the patient's cells. Because the patient's cells lack the rep and cap genes and the helper virus accessory function genes, the rAAV are replication defective; that is, they cannot further replicate and package their genomes. Similarly, without a source of rep and cap genes, wild-type AAV cannot be formed in the patient's cells. See, e.g., U.S. Pat. No. 6,001,650 to Colosi, issued Dec. 14, 1999.

Nonviral methods for introducing DNA into cells and tissues have also been described. Such methods include calcium phosphate co-precipitation, Graham et al., *Virol.* 52:456–467 (1973), direct micro-injection into cells, Capecchi, *Cell* 22:479–488 (1980), liposome-mediated gene transfer, Mannino et al., *BioTechniques* 6:682–690 (1988), lipid-mediated transfection, Felgner et al., *Proc. Natl. Acad. Sci. USA* 84:7413–7417 (1987), and nucleic acid delivery using high-velocity microprojectiles, Klein et al., *Nature* 327:70–73 (1987). In vivo electroporation methods for introducing DNA into cells and tissues have also been described. See, e.g., Shigekawa et al., *BioTechniques* 6:742–751 (1988); Mathiesen, *Gene Therapy* 6:508–514 (1999) (describing the effects of electropermeabilization of skeletal muscle on gene transfer). Recombinantly produced proteins and synthetic fusions may also be introduced into cells by protein transduction techniques. See Schwarze et al., *Science* 285:1569–1572 (1999).

One of skill in the art would recognize that genes encoding the SID linked to a DNA-binding peptide, having already been introduced into a patient's cells using either viral or non-viral methods, may be operably linked to control elements such as promoters and enhancers that are capable of driving gene expression in the patient's neurons under appropriate conditions. Termination signals, such as polyadenylation sites, can also be included. Control elements (such as inducible promoters) are available that allow controlled expression of the gene of interest. For example, an ecdysone-inducible promoter may be used to allow regulated expression of the integrin gene. See, e.g., *Stratagene's Complete Control™ Inducible Mammalian Expression System Instruction Manual* (available online at http://www.stratagene.com/manuals/index.shtm). Other small molecule-inducible promoters that are functional in mammalian cells include those that are induced (or repressed) by tetracycline and its derivatives, RU486, and rapamycin and its derivatives. See, e.g., Grossen & Brujard, *Proc. Natl. Acad. Sci. USA* 89:5547–5551 (1992); Wang et al., *Gene Therapy* 4:432–441 (1997); Rivera et al., *Nature Medicine* 2:1028–1032 (1996). Such inducible promoters could provide the ability to confer transcriptional repression at any stage of development, or at any time chosen by the user.

EXAMPLES

The following examples are given to illustrate various embodiments which have been made within the scope of the present invention. It is to be understood that the following examples are neither comprehensive nor exhaustive of the many types of embodiments which can be prepared in accordance with the present invention.

Example 1
Mad1 and mSin3A Interact Directly

The abbreviations used herein are: HDAC1, histone deacetylase 1; HDAC2, histone deacetylase 2; bHLHZip, basic region-helix-loop-helix-zipper; SID, mSin3 interaction domain; PAH, paired amphipathic helix; CD, circular dichroism; TFE, trifluoroethanol; PBS, phosphate-buffered saline; GST, glutathione S-transferase; PVDF, polyvinylidene fluoride; GALDBD, GAL4 DNA binding domain; KID, kinase-inducible domain; deg, degree(s); PAGE, polyacrylamide gel electrophoresis.

Experimental Procedures. The experimental procedures employed in these Examples are as follows:

Cloning and Interaction Assays—Fusions to the LexA DNA binding domain were made either by polymerase chain reaction amplifying SID 1–57 and SID 1–27 using pSPMad1 or pSPMad1 (L12P/A16P) (Ayer et al., *Cell* 80:767–776 (1995)) as template or by inserting a double-stranded oligonucleotide cassette encoding the various SID constructs between the EcoRI and BamH1 sites of pBTM116. Hollenberg et al., *Mol. Cell. Biol.* 15:3813–3822 (1995). Each construct was verified by sequencing. The different LexA fusion constructs and VP16PAH2 (Ayer et al., *Cell* 80:767–776 (1995)) were introduced into the *S. cerevisiae* strain L40 by lithium acetate transformation. Ausubel et al. eds., *Current Protocols in Molecular Biology*, John Wiley & Sons, Inc., New York (1995). Quantitative β-galactosidase assays were performed from three independent colonies in triplicate from liquid cultures. Ausubel et al. eds., *Current Protocols in Molecular Biology*, John Wiley & Sons, Inc., New York (1995). For each measurement the standard deviation was less than 10%.

Transcription Assays—293 cells were grown in Dulbecco's modified Eagle's medium with 10% defined calf serum (HyClone). $2 \times 10^5$ cells were planted on 60-mm dishes and transfected with 200 ng of the Gal4-14D luciferase reporter (Ayer et al., *Mol. Cell Biol.* 16:5772–5781 (1996)) and 1 μg of the indicated expression vector. Cells harvested 24 h after transfection and luciferase and β-galactosidase activity measured according to the manufacturers' protocols (Promega and Tropix). Each transfection was performed at least twice in triplicate. Error shown is the standard of the mean.

Peptide Synthesis—The four SID-containing peptides were synthesized and purified by the Huntsman Cancer Institute DNA/Peptide Resource Core Facility. Each peptide includes residues 7–20 of human Mad1. The sequence of the wild-type SID peptide is GGGM-NIQMLLEAADYLE (SEQ ID NO: 24). The sequence of the double mutant L12P/A16P SID is GGGMNIQM-PLEAPDYLE (SEQ ID NO: 25). The sequences of the two single mutant peptides A15D SID and L19D SID are GGGMNIQMLLEDADYLE (SEQ ID NO: 26) and GGGMNIQMLLEAADYDE (SEQ ID NO: 27), respectively. Peptide concentrations were determined by measuring the absorbance of the peptide at 280 nm and using the extinction coefficient for a single tyrosine of $1.49 \times 10^3$ $M^{-1}$ $cm^{-1}$.

Circular Dichroism (CD) Spectroscopy—CD samples contained 50 μM of peptide, 1×phosphate-buffered saline, and the percentage of trifluoroethanol (TFE, Sigma) indicated in FIG. 4. CD spectra were collected on an Aviv 62DS spectrophotometer from 280 to 195 nm at 25° C. using a cell with a 0.1-cm pathlength. The reported spectra are the average of 15 consecutive runs. The observed ellipticity was converted to mean residue molar ellipticity [Θ] (deg $cm^2$ $dmol^{-1}$) using the relationship $[\Theta]=\Theta/(C_r \cdot 1)$ where Θ is the observed ellipticity, 1 is the pathlength, and $C_r$ is the mean residue molar concentration. Fractional helicities were calculated as described using values for $[\Theta]^0{}_{222}$ and $[\Theta]^{100}{}_{222}$, corresponding to 0% and 100% helical content at 222 nm, of −2000 and −28,400 deg $cm^2$ $dmol^{-1}$, respectively. Wu et al., *Biochemistry* 20:5766–570 (1981).

Far Western Blotting—Mad1His and Mad1(L12P/A16P)His (Ayer et al., *Cell* 80:767–776 (1995)), which have a polyhistidine tag fused to their carboxyl termini, were translated in vitro in 50 μl reactions using the TNT coupled reticulocyte lysate system (Promega) and $^{35}[S]$ methionine (NEN Life Science Products) and were purified under native or denaturing conditions. $Ni^{2+}$-NTA agarose (Qiagen) was blocked with rabbit reticuocyte lysate (diluted 1:3 in PBS) for 30 min at 4° C. and then incubated with the in vitro synthesized Mad1His and Mad1(L12P/A16P)His for 30 min at 4° C. in PBS native or 6 M guanidine hydrochloride, 0.1 M $NaH_2PO_4$, and 0.01 M Tris, pH 8.0 (denaturating conditions) followed by extensive washing with the same buffers. The bound proteins were eluted in PBS containing 0.5 M imidazole and then dialyzed overnight against PBS to remove the imidazole and allow for renaturation. Recombinant GST and GST-PAH2 were expressed in bacteria and purified on glutathione-Sepharose 4B (Amersham Pharmacia Biotech). The blots were prepared by resolving 1 μg of GST-PAH2 on 15% SDS-PAGE, followed by transfer to PVDF membrane. The blots were blocked in far Western Buffer (PBS containing 0.1% Nonidet P-40, 1 mM EDTA, and 1 mM dithiothreitol) containing 5% nonfat dry milk for 1 h at 4° C. Purified probes were added to blots in 5 ml of far Western buffer containing 1% nonfat dry milk and incubated together at 4° C. overnight with rocking. Following washing with far Western buffer, the blots were air-dried and exposed 48 h for autoradiography.

Results

It had not been conclusively demonstrated that the interaction between mSin3A and Mad1 is direct. For example, the interaction between Mad1 and mSin3A has been detected using the two-hybrid assay, in vitro translated proteins, and co-immuno-precipitation from cell extracts containing epitope-tagged Mad1. Laherty et al., *Cell* 89:349–356 (1997), Ayer et al., *Cell* 80: 767–776 (1995), and Schreiber-Angus et al., Cell 80:777–786 (1995). While these experiments suggests that the interaction between Mad1 and mSin3A is direct, they do not rule out the possibility that a bridging factor could mediate the interaction between Mad1 and mSin3A.

To determine whether the interaction between Mad1 and mSin3A is direct, we used far Western blot assays. In these experiments GST-PAH2, a GST fusion to the PAH2 domain of mSIN3A, and GST alone were resolved by SDS-PAGE followed by transfer to a PVDF membrane. Duplicate blots were probed with $^{35}$S-labeled in vitro transcribed and translated Mad1His and mutant Mad1 protein, Mad1 (L12P/A16P)His, that does not interact with mSin3A. Equal efficiency of transcription and translation of these proteins was confirmed by SDS-PAGE followed by autoradiography to detect the proteins (data not shown). These protein probes were purified on $Ni^{2+}$-NTA agarose under native or denaturing conditions. When purified under native conditions, Mad1His but not Mad1(L12P/A16P)His was able to interact with GST-PAH2. Neither Mad1His nor Mad1 (L12P/A16P) His interacted with GST alone (FIG. 1A). Together, these results confirm that Mad1 interacts specifically with PAB2 of mSin3A and that the interaction is sensitive to mutations in the SID. However, because there is abundant mSin3A and presumably interacting cofactors, in reticulocyte lysate (data not shown), the possibility exists that a bridging factor may have copurified with Mad1 under native conditions and that it mediated the interaction between Mad1 and PAH2. Mad1His purified under denaturing conditions and subsequently renatured also interacted with GST-PAH2 but not with GST alone (FIG. 1B, left panel). Furthermore, Mad1 (L12P/A16P)His purified under denaturing conditions did not interact with either GST or GST-PAH2 (FIG. 1B, right panel). It is very likely that any interaction between Mad1 and a putative bridging factor would have been disrupted under the denaturing conditions used for purification. Therefore, these results indicate that the interaction between Mad1 and PAH2 of mSin3A is direct and does not require a bridging factor.

Example 2

The SID is an Amphipathic Helix

Alignment of the Mad family proteins and Mnt from different species reveals that amino acids 7–35, numbering relative to Mad1, are highly conserved (FIG. 2A). Within this block of residues, the sequence LLEAA (residues 6–10 of SEQ ID NO: 2) is nearly identical between the aligned molecules, suggesting that it may form the core of the interaction domain. This block of conservation is followed by a stretch of charged amino acids and the sequence EHGYAS (residues 21–26 of SEQ ID NO: 2). These downstream sequence elements are highly conserved within the mammalian Mad proteins but are absent from the Mnt proteins and an invertebrate Mad homologue. Previous mutagenesis studies in which the first 35 amino acids of Mad1 were deleted have demonstrated that this conserved amino-terminal region is necessary for interaction between Mad proteins and mSin3A. Ayer et al., *Cell* 80:767–776 (1995). Another Mad1 truncation in which the first 20 amino acids of Mad1 are deleted but leaves the EHGYAS (residues 21–26 of SEQ ID NO: 2) region intact was also tested. This deletion was also unable to interact with mSin3A, indicating that the conserved EHGYAS (residues 21–26 of SEQ ID NO: 2) region is not sufficient for the Mad1:mSin3A interaction. Ayer et al., *Cell* 80:767–776 (1995). Further, experiments have shown that amino acids 1–35 of Mad1 mediate histone deacetylase-dependent repression. Hassig et al., *Cell* 89:341–347 (1997), Laherty et al., *Cell* 89:349–356 (1997), Ayer et al., *Cell* 80:767–776 (1995), Hurlin et al., *EMBO J.* 14:5646–5659 (1995), Hurlin et al., *Genes Dev.* 11:44–58 (1997). However, the minimal domain required for the interaction between Mad1 and mSin3A and the role, if any, of the conserved EHGYAS (residues 21–26 of SEQ ID NO: 2) region in this interaction have not been determined.

We have used a directed two-hybrid assay to measure the relative affinity of the SID and various SID mutants for PAH2. Briefly, SID molecules based on the sequence of human Mad1 were fused to the DNA binding domain of bacterial LexA, and the PAH2 domain of mSin3A was fused to the transcriptional activation domain of VP16. Following introduction into the *S. cerevisiae* strain L40, relative affinity was measured by quantitative analysis of the β-galactosidase activity generated from an integrated LexA-dependent LacZ reporter gene.

To define the minimal sequence required for interaction with PAH2, we constructed a series of amino- and carboxyl-terminal truncations of the SID. Consistent with previous findings (Ayer et al., *Cell* 80:767–776 (1995)), the region from the initiating methionine to the beginning of the basic region, amino acids 1–57, was sufficient for interaction and two point mutations within the putative α-helical region of the SID, L12P/A16P, completely abolished interaction (FIG. 2B). A carboxyl-terminal deletion of 30 amino acids, SID 1–27, which removes the conserved EHGYAS (residues 21–26 of SEQ ID NO: 2), bound PAH2 almost 2-fold better than the longer amino-terminal construct, suggesting that the EHGYAS sequence (residues 21–26 of SEQ ID NO: 2) has a slight negative effect on binding (FIG. 2B). Again, in the context of this protein, the L12P/A16P double mutation completely abolished interaction. Further deletion analysis demonstrated that amino acids 8–20 are necessary and sufficient for interaction. These findings suggest that the highly conserved region between amino acids 20–35 found in the vertebrate Mad proteins is completely dispensable for interaction and that the sequences that are conserved between Mad proteins across species and Mnt constitute a minimal SID.

To determine which residues of the minimal SID are required for interaction with PAH2, we first displayed residues 7–20 on a helical wheel (FIG. 3A). This conceptual α-helix is amphipathic. The three residues that are less conserved within the Mad family and Mnt, positions Gln-10, Glu-14 and Asp-17, all lie on the hydrophilic face of the α-helix. Given the charged nature of the hydrophilic face and the lower conservation of Gln-10, Glu-14, and Asp-17, this surface is predicted not to be involved in the SID:PAH2 interaction. In contrast, the highly conserved hydrophobic face of this putative α-helix is predicted to mediate protein-protein interaction. To determine which face of the SID is required for interaction with PAH2, we mutated several amino acids in the context of the minimal thirteen amino acid SID (FIG. 3B). As predicted, mutation of the presumptive face had little effect on interaction. A SID peptide containing a QLOR mutation reduced binding 4-fold, while three single mutations to alanine, Q10A, E14A, and D17A, could bind to PAH2 with approximately 2-fold higher affinity. A protein containing all three alanine mutations (Q10A/E14A/D17A) bound PAH2 with affinity similar to each of the single alanine mutants, further supporting the hypothesis that these residues are not involved in the interaction. In addition, because alanine substitutions are thought to be compatible with helical structure, this finding is consistent with the predicted helicity of the SID.

Mutation of any of the presumptive contact hydrophobic residues, Ala-15, Tyr-18, or Leu-19, to aspartic acid severely impaired binding. Our original double mutant, L12P/A16P (Ayer et al., Cell 80:767–776 (1995)), failed to interact with PAH2, suggesting that these residues may be involved in direct contact between the SID and PAH2. Alternatively, it is possible that the double proline mutations disrupt the helical nature of the SID and the mutant fails to interact for this reason. To further test whether these residues are involved directly in the interaction, amino acids 12 and 16 were mutated in tandem to glutamic and aspartic acid, respectively. We predicted that these alterations would not disrupt the helical nature of the SID, but would no longer make hydrophobic interactions. Like the single mutants at the presumptive contact interface, this double mutant was incapable of high affinity interaction with PAH2. This mutational analysis is consistent with the hypothesis that the SID forms an amphipathic α-helix with the hydrophobic face serving as the contact interface with PAH2.

Figure 4A:
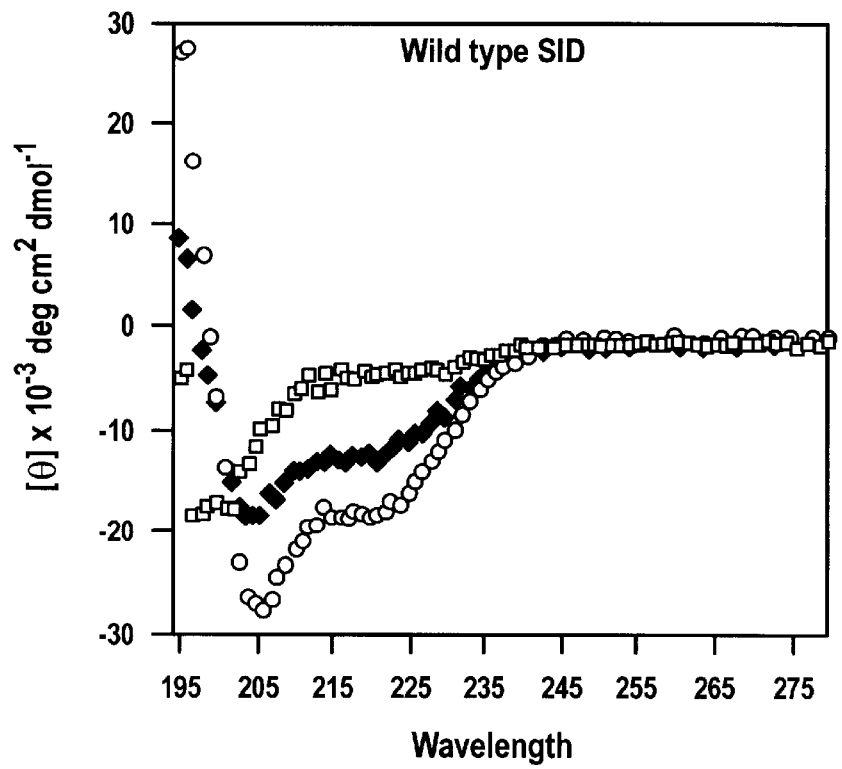
FIGS. 4A and 4B show that the wildtype SID peptide has an inherent helical propensity. The CD spectra of wildtype SID and L12P/A16P SID peptides were measured in 1, 20, and 50% TFE. The CD spectra of the wildtype SID peptide (4A) and the L12P/A16P SID peptide (4B) are shown. Percentages of TFE are denoted as follows: □=1% TFE, ◆=20% TFE, and ●=50% TFE.

To test directly if the SID could adopt an α-helical structure, we measured the helical content of wild-type SID and mutant SID peptides using circular dichroism (CD) spectroscopy. Short peptides do not generally form secondary structures in aqueous solutions because the solvent competes for structure-stabilizing intramolecular hydrogen bonds. Therefore, spectra for the wild-type and mutant SID peptides were measured in the solvent TFE, which is commonly used to stabilize α-helical conformation in peptides that have an inherent helical propensity. Sonnichsen et al., Biochemistry 31 :8790–8798 (1992), Jasanoff and Fersht, Biochemistry 33:2129–2135 (1994). In an aqueous solution containing 1% TFE, the wild-type SID peptide lacks secondary structure (FIG. 4A). At increasing TFE concentrations, the wild-type peptide adopts an α-helical structure as indicated by the strong negative peaks at 208 and 222 nm. In 20% TFE the SID is approximately 40% α-helical. This percentage increases to approximately 60% in 50% TFE. Thus, as predicted the wild-type SID has helical propensity and is able to adopt an α-helical conformation.

Figure 4B:
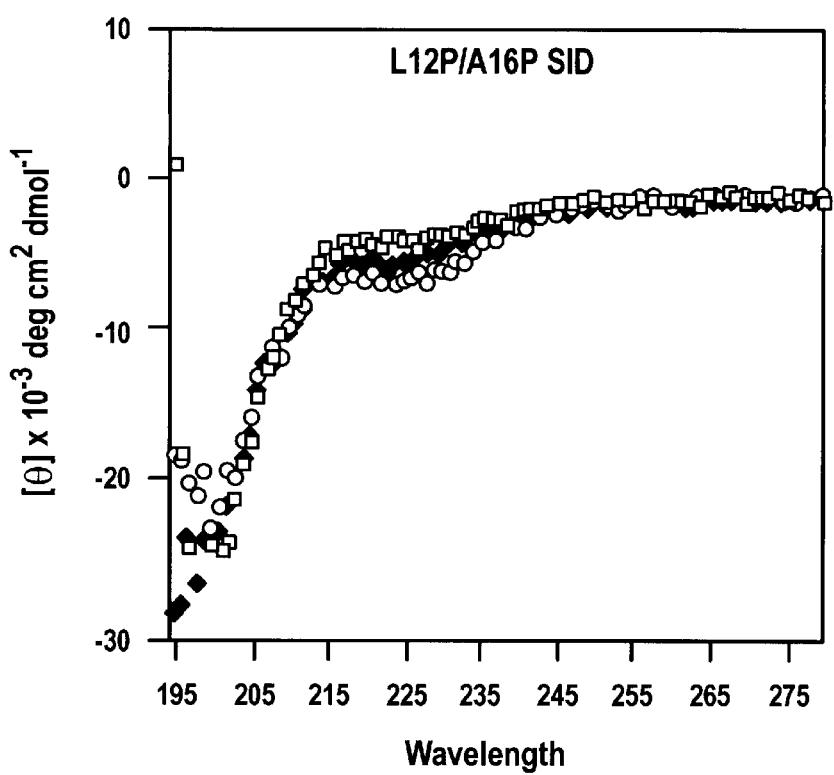

Recently, it was demonstrated that TFE destabilizes the unfolded state of a peptide that indirectly enhances the folding of the helix. Kentsis and Sosnick, Biochemistry 37:14613–14622 (1998). Therefore, we were concerned that any peptide, regardless of its inherent helical content, might be forced into a helical structure at high TFE concentrations. Unlike the wild-type SID, however, the spectra of a SID peptide with two putative α-helix-destabilizing proline substitutions, L12P/A16P, remained unchanged with increasing concentrations of TFE, demonstrating that it does no undergo a transition from random coil to α-helix (FIG. 4B). We infer that the α-helical structure observed with the wild-type SID peptide in TFE is a reflection of its helical propensity. These results, along with those from the directed two-hybrid assay, suggest that the SID must adopt an α-helical conformation to allow interaction with PAIH2.

Figure 5A:
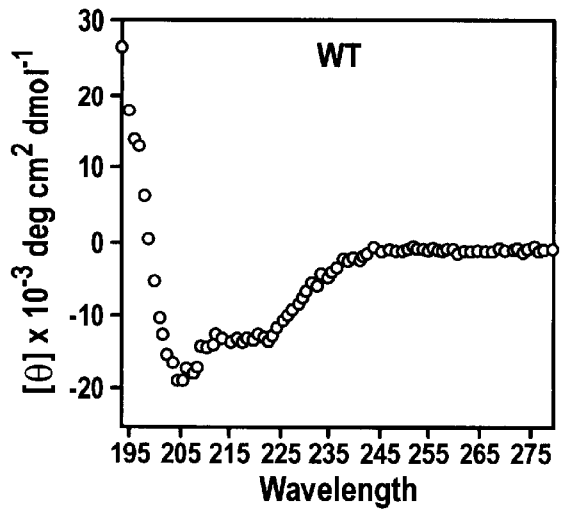
FIGS. 5A and 5B demonstrate that mutant SIDs that are unable to interact with PAH2 have an inherent helical propensity. The CD spectra of wildtype SID peptide (5A), A15D SID peptide (5B), and L19D SID peptide (5C) measured in 50% TFE are shown.
Figure 5B:
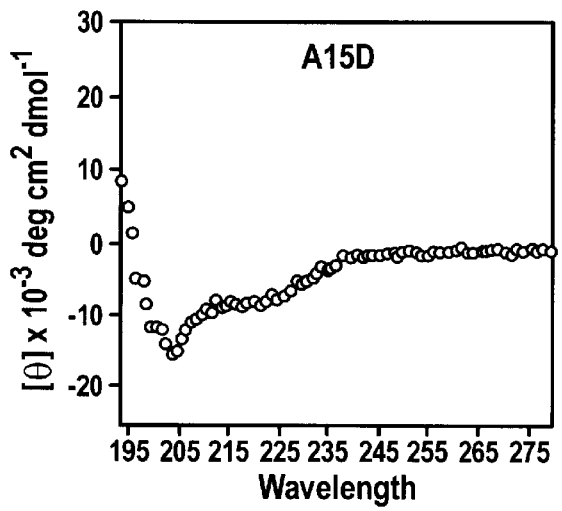
Figure 5C:
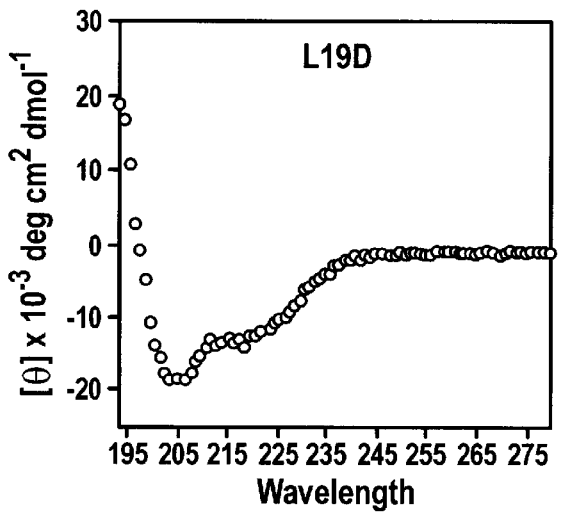

The SID mutant L12E/A16D is unable to interact with PAH2 (FIG. 3B). We hypothesized that, unlike the helix-destabilizing proline substitutions, this mutant peptide's loss of binding may have resulted from disruption of hydrophobic interactions required for contact with PAH2 rather than disruption of helical structure. However, the CD spectrum of L12E/A16D SID indicates that in 50% TFE this peptide in not as helical as the wild-type peptide and shows only slightly more helical nature than L12P/A16P SID (data not shown). Thus, these mutations appear to affect the structure of the SID, making it impossible to discern whether the inability of this mutant to interact with PAH2 in the two-hybrid is due to disruption of hydrophobic interactions or the disruption of secondary structure. In an attempt to clarify the role of the hydrophobic residues of the SID, we collected the CD spectra for the two single mutant peptides, A15D SID and L19D SID. The spectrum for L19D SID was nearly identical to that collected for the wild-type SID, while the spectrum for A15D showed that it was slightly less helical than the wild-type SID, indicating that both mutant peptides are primarily helical in 50% TFE (FIG. 5, A–C). Calculation of percentage helicity for the peptides indicated that the mutations A15D and L19D reduced the helicity, of the SID relative to wild-type, by approximately 40% and 5%, respectively. Therefore, A15D SID and L19D SID retain helical structure but are unable to interact with PAH2 in the two-hybrid. This suggests that the hydrophobic face of the SID α-helix, which is disrupted in these mutants, is important for interaction with PAH2.

Example 3

Amino Acids 8–20 of Mad1 Function as a Portable Repressor Domain

Figure 6A:
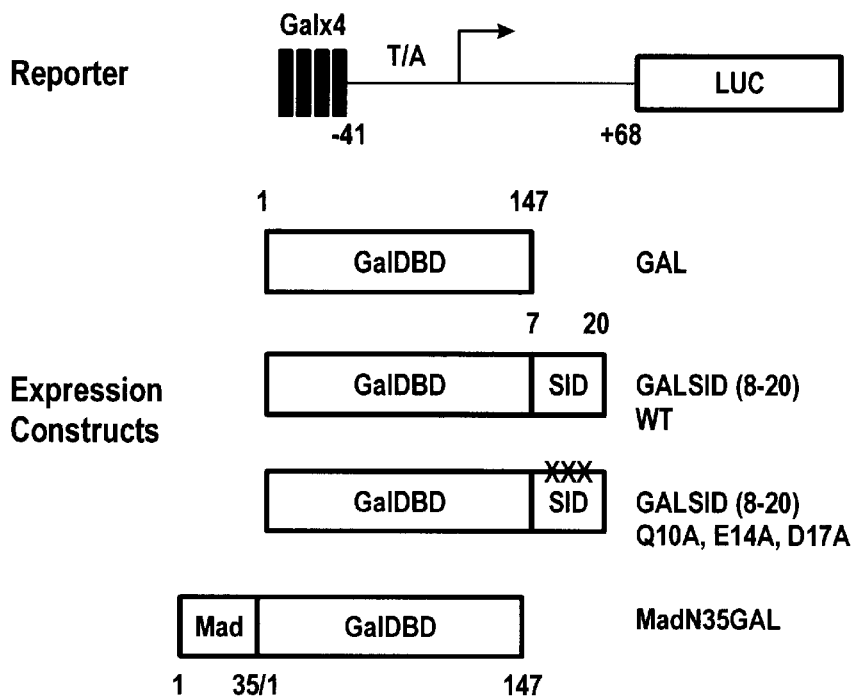
FIGS. 6A and 6B illustrate how SID 8–20 functions as a portable repression domain. The reporter plasmid and expression vectors used in this experiment are shown in FIG. 6A. Transcriptional activity of the GAL4 DNA binding domain-responsive reporter in the presence of the expression vectors is indicated at the bottom of the figure. LUC, luciferase; RLU, relative light units, in FIG. 6B.
Figure 6B:
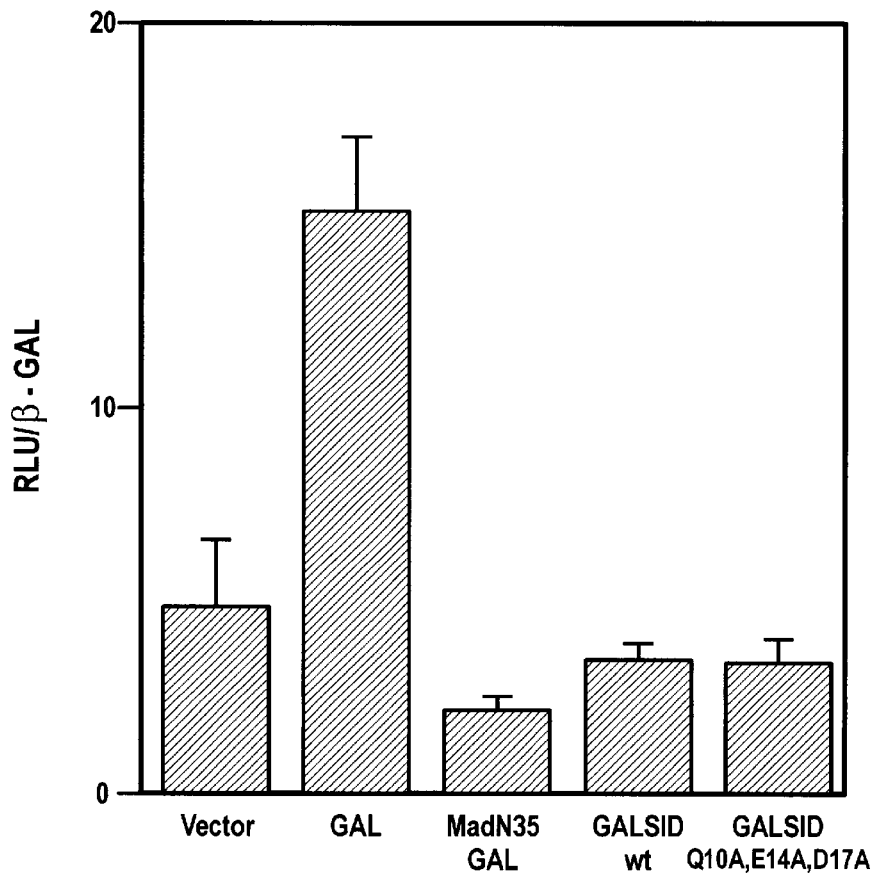
Figure 7A:
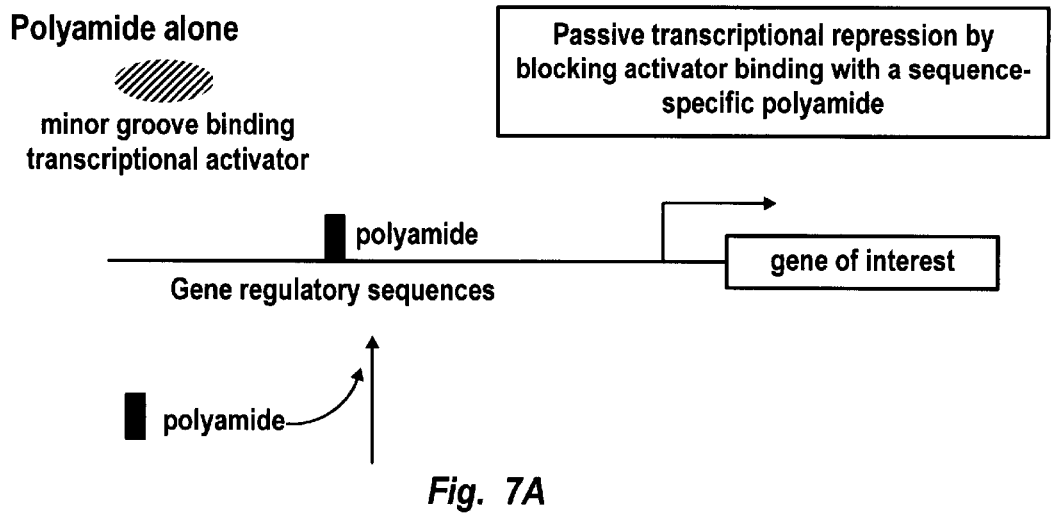
FIGS. 7A–7C schematically illustrates the transcriptional repressive effects of a polyamide alone (FIG. 7A), unrepressed transcriptional activation (FIG. 7B), and the effects of using a SID-polyamide chimera (FIG. 7C). When sequence-specific polyamides are present, transcriptional repression may result due to passive blocking of activator binding. In contrast, the use of a SID-polyamide chimera causes active repression of transcription by a modification of the chromatin structure by the mSIN3A/HDAC complex.
Figure 7B:
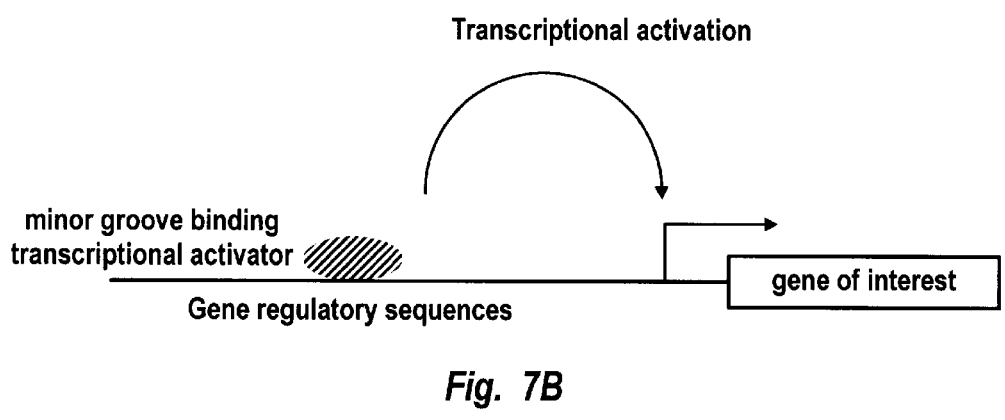
Figure 7C:
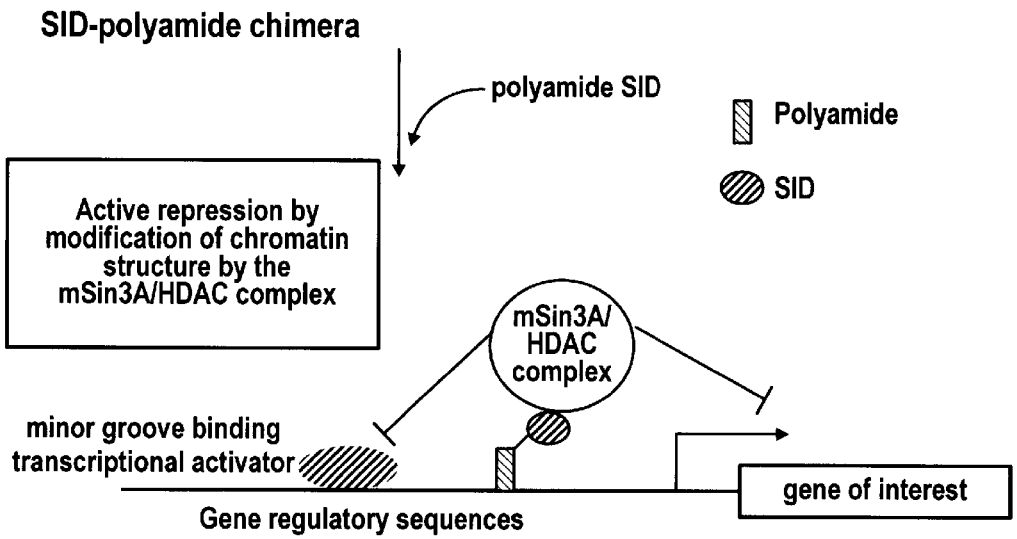

Our mutational analysis suggests that a thirteen amino acid amphipathic α-helix mediates the interaction between the SID and PAH2. To test whether this minimal thirteen residue interaction domain is sufficient to target a functional mSin3:HDAC corepressor complex to DNA, we fused amino acids 8–20 from Mad1 to the DNA binding domain of the yeast transcriptional activator GAL4 (GALDBD). The transcriptional activity of GALSID(8–20) WT was tested on a reporter containing four GAL4 binding sites cloned upstream of a minimal promoter (FIG. 6A). Consistent with our previous findings (Ayer et al., Mol. Cell. Biol. 16:5772–5781 (1996)), the GALDBD alone activates this reporter approximately 3-fold, and a fusion between the first 35 amino acids of Mad1 and the GALDBD repressed this level of reporter activity approximately 7-fold. GALSID (8–20) WT repressed transcription to approximately the same level when fused to the GAL4 DNA binding domain (FIG. 6B), suggesting that this minimal SID is sufficient to target functional mSin3-HDAC complexes to DNA. Amino acids 10, 14, and 17 of the SID can be mutated to alanine without adversely affecting the interaction with PAH2 (FIG. 3). However, it is possible that these residues constitute a surface that interacts with other components of the mSin3-HDAC complex and/or components of the general transcriptional machinery. To test whether mutation of these residues may impair the ability of the SID to recruit a functional corepressor complex, we constructed a minimal SID containing the mutations Q10A, E14A, and D17A in the context of a GALDBD fusion (FIG. 6A). This mutant SID (GALSID Q10A, E14A, D17A) repressed transcription to the same extent as the wild-type minimal SID (FIG. 6B), suggesting that the surface comprised of residues 10, 14, and 17 is unlikely to make functionally important contacts with other components of the mSin3A-HDAC complex.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A chimeric transcriptional regulator comprising a DNA-binding domain and a mSin3A Interaction Domain (SID) capable of binding mSin3A, wherein the SID consists of an amino acid sequence with at least about 10 of 13 amino acids identical to the amino acid sequence of SEQ ID NO. 1.

2. The chimeric transcriptional regulator of claim 1, wherein the SID consists of an amino acid sequence with at least about 11 of 13 amino acids identical to the amino acid sequence of SEQ ID NO: 1.

3. The chimeric transcriptional regulator of claim 1, wherein the SID consists of an amino acid sequence with at least about 12 of 13 amino acids identical to the amino acid sequence of SEQ ID NO: 1.

4. The chimeric transcriptional regulator of claim 1, wherein the SID consists of an amino acid sequence that is identical to the amino acid sequence of SEQ ID NO: 1.

5. The chimeric transcriptional regulator of claim 1, wherein the SID consists of an amino acid sequence that is at least about 77% identical to the amino acid sequence of SEQ ID NO: 1.

6. The chimeric transcriptional regulator of claim 2, wherein the SID consists of an amino acid sequence that is at least about 85% identical to the amino acid sequence of SEQ ID NO: 1.

7. The chimeric transcriptional regulator of claim 3, wherein the SID consists of an amino acid sequence that is at least about 92% identical to the amino acid sequence of SEQ ID NO: 1.

8. A fusion comprising a mSin3A Interaction Domain (SID) capable of binding mSin3A, wherein the SID consists of an amino acid sequence with at least about 10 of 13 amino acids identical to the amino acid sequence of SEQ ID NO: 1 and wherein the SID is linked to a DNA-binding molecule.

9. The fusion of claim 8, wherein the DNA-binding molecule comprises a polyamide.

10. The fusion of claim 8, wherein the DNA-binding molecule comprises a zinc-finger domain capable of recognizing a DNA sequence.

11. The fusion of claim 8, wherein the SID consists of an amino acid sequence that is at least about 77% identical to the amino acid sequence of SEQ ID NO: 1 and wherein the SID is linked to a DNA-binding molecule.

12. The fusion of claim 9, wherein the polyamide is capable of binding a regulatory region of a gene.

13. The fusion of claim 10, wherein the zinc finger domain is capable of recognizing a regulatory region of a gene.

14. A method of creating a transcriptional regulator comprising:
 a. synthesizing an mSin3A-binding molecule consisting of an amino acid sequence with at least about 10 of 13 amino acids identical to the amino acid sequence of SEQ ID NO: 1; and
 b. linking the mSin3A-binding molecule to a heterologous DNA-binding molecule.

15. The method of claim 14, wherein the mSin3A-binding molecule consists of an amino acid sequence with at least about 11 of 13 amino acids identical to the amino acid sequence of SEQ ID NO: 1.

16. The method of claim 10, wherein the mSin3A-binding molecule consists of an amino acid sequence with 12 of 13 amino acids identical to the amino acid sequence of SEQ ID NO: 1.

17. The method of claim 14, wherein the DNA-binding molecule comprises a polyamide capable of recognizing a regulatory DNA sequence.

18. The method of claim 14, wherein the DNA-binding molecule comprises a zinc finger domain capable of recognizing a regulatory DNA sequence.

19. The method of claim 14, wherein the linking is accomplished by direct synthesis.

20. The method of claim 14, wherein the linking is accomplished using recombinant DNA technology.

21. The method of claim 14, wherein the linking is accomplished by biotin-streptavidin interactions.

22. The method of claim 14, wherein the linking is accomplished using conditional dimerization technology.

23. The method of claim 14, wherein the mSin3A-binding molecule consists of an amino acid sequence identical to the amino acid sequence of SEQ ID NO: 1.

24. The method of claim 15, wherein the mSin3A-binding molecule consists of an amino acid sequence at least about 82% identical to the amino acid sequence of SEQ ID NO: 1.

25. The method of claim 16, wherein the mSin3A-binding molecule consists of an amino acid sequence at least about 92% identical to the amino acid sequence of SEQ ID NO: 1.

26. The method of claim 22, wherein the linking is accomplished using FK506 and FKBP interactions.

* * * * *

SEQUENCE LISTING

```
<160> NUMBER OF SEQ ID NOS:  27

<210> SEQ ID NO 1
<211> LENGTH: 13
<212> TYPE: PRT
<213> ORGANISM: Homo sapiens

<400> SEQUENCE: 1

Asn Ile Gln Met Leu Leu Glu Ala Ala Asp Tyr Leu Glu
  1               5                  10

<210> SEQ ID NO 2
<211> LENGTH: 29
<212> TYPE: PRT
<213> ORGANISM: Mus musculus

<400> SEQUENCE: 2

Met Asn Ile Gln Leu Leu Leu Glu Ala Ala Asp Tyr Leu Arg Arg
  1               5                  10                  15

Glu Arg Glu Ala Glu His Gly Tyr Ala Ser Met Leu Pro
             20                  25

<210> SEQ ID NO 3
<211> LENGTH: 29
<212> TYPE: PRT
<213> ORGANISM: Homo sapiens

<400> SEQUENCE: 3

Met Asn Ile Gln Met Leu Leu Glu Ala Ala Asp Tyr Leu Arg Arg
  1               5                  10                  15

Glu Arg Glu Ala Glu His Gly Tyr Ala Ser Met Leu Pro
             20                  25

<210> SEQ ID NO 4
<211> LENGTH: 29
<212> TYPE: PRT
<213> ORGANISM: Mus musculus

<400> SEQUENCE: 4

Asn Ser Leu Leu Leu Leu Leu Glu Ala Ala Glu Tyr Leu Glu Arg Arg
  1               5                  10                  15

Asp Arg Glu Ala Glu His Gly Tyr Ala Ser Met Leu Pro
             20                  25

<210> SEQ ID NO 5
<211> LENGTH: 29
<212> TYPE: PRT
<213> ORGANISM: Homo sapiens

<400> SEQUENCE: 5

Asn Ser Leu Leu Ile Leu Leu Glu Ala Ala Glu Tyr Leu Glu Arg Arg
  1               5                  10                  15

Asp Arg Glu Ala Glu His Gly Tyr Ala Ser Val Leu Pro
             20                  25

<210> SEQ ID NO 6
<211> LENGTH: 29
```

```
<212> TYPE: PRT
<213> ORGANISM: Mus musculus

<400> SEQUENCE: 6

Ser Asn Ile Gln Val Leu Leu Gln Ala Ala Glu Phe Leu Glu Arg Arg
 1               5                  10                  15

Glu Arg Glu Ala Glu His Gly Tyr Ala Ser Leu Cys Pro
            20                  25

<210> SEQ ID NO 7
<211> LENGTH: 29
<212> TYPE: PRT
<213> ORGANISM: Homo sapiens

<400> SEQUENCE: 7

Ile Asn Val Gln Arg Leu Leu Glu Ala Ala Glu Phe Leu Glu Arg Arg
 1               5                  10                  15

Glu Arg Glu Cys Glu His Gly Tyr Ala Ser Ser Phe Pro
            20                  25

<210> SEQ ID NO 8
<211> LENGTH: 29
<212> TYPE: PRT
<213> ORGANISM: Mus musculus

<400> SEQUENCE: 8

Ile Asn Val Gln Arg Leu Leu Glu Ala Ala Glu Phe Leu Glu Arg Arg
 1               5                  10                  15

Glu Arg Glu Cys Glu His Gly Tyr Ala Ser Ser Phe Pro
            20                  25

<210> SEQ ID NO 9
<211> LENGTH: 32
<212> TYPE: PRT
<213> ORGANISM: Zebrafish

<400> SEQUENCE: 9

Lys Asn Val Gln Val Leu Leu Glu Ala Ala Ser Tyr Ile Glu Ser Ala
 1               5                  10                  15

Glu Arg Lys Asp Gly Lys Cys Glu His Gly Tyr Ala Ser Thr Phe Pro
            20                  25                  30

<210> SEQ ID NO 10
<211> LENGTH: 25
<212> TYPE: PRT
<213> ORGANISM: Homo sapiens

<400> SEQUENCE: 10

Met Ser Ile Glu Thr Leu Leu Glu Ala Ala Arg Phe Leu Glu Trp Gln
 1               5                  10                  15

Ala Gln Gln Gln Gln Arg Ala Arg Glu
            20                  25

<210> SEQ ID NO 11
<211> LENGTH: 25
<212> TYPE: PRT
<213> ORGANISM: Mus musculus

<400> SEQUENCE: 11

Met Ser Ile Glu Thr Leu Leu Glu Ala Ala Arg Phe Leu Glu Trp Gln
 1               5                  10                  15

Ala Gln Gln Gln Gln Arg Ala Arg Glu
```

```
                        20                  25

<210> SEQ ID NO 12
<211> LENGTH: 18
<212> TYPE: PRT
<213> ORGANISM: Caenorhabditis elegans

<400> SEQUENCE: 12

Asn Leu Gly His Leu Leu Thr Ala Ala Arg Leu Leu Asp Ile Gly Ala
  1               5                  10                  15

Leu Asp

<210> SEQ ID NO 13
<211> LENGTH: 27
<212> TYPE: PRT
<213> ORGANISM: Homo sapiens

<400> SEQUENCE: 13

Met Ala Ala Ala Val Arg Met Asn Ile Gln Met Leu Leu Glu Ala Ala
  1               5                  10                  15

Asp Tyr Leu Glu Arg Arg Glu Arg Glu Ala Glu
            20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 14

Met Ala Ala Ala Val Arg Met Asn Ile Gln Met Pro Leu Glu Ala Pro
  1               5                  10                  15

Asp Tyr Leu Glu Arg Arg Glu Arg Glu Ala Glu
            20                  25

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 15

Asn Ile Arg Met Leu Leu Glu Ala Ala Asp Tyr Leu Glu
  1               5                  10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 16

Asn Ile Ala Met Leu Leu Glu Ala Ala Asp Tyr Leu Glu
  1               5                  10

<210> SEQ ID NO 17
<211> LENGTH: 13
<212> TYPE: PRT
<213> ORGANISM: Artificial Sequence
```

```
<220> FEATURE:
<223> OTHER INFORMATION: Description of Artificial Sequence:Mutant human
      Mad1 peptide sequence.

<400> SEQUENCE: 17

Asn Ile Gln Met Leu Leu Ala Ala Ala Asp Tyr Leu Glu
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 18

Asn Ile Gln Met Leu Leu Glu Ala Ala Ala Tyr Leu Glu
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 19

Asn Ile Ala Met Leu Leu Ala Ala Ala Ala Tyr Leu Glu
 1               5                  10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 20

Asn Ile Gln Met Glu Leu Glu Ala Asp Asp Tyr Leu Glu
 1               5                  10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 21

Asn Ile Gln Met Leu Leu Glu Asp Ala Asp Tyr Leu Glu
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 22

Asn Ile Gln Met Leu Leu Glu Ala Ala Asp Asp Leu Glu
 1               5                  10
```

```
<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence:Mutant human
      Mad1 peptide sequence.

<400> SEQUENCE: 23

Asn Ile Gln Met Leu Leu Glu Ala Ala Asp Tyr Asp Glu
 1               5                  10

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:Synthetic
      peptide.

<400> SEQUENCE: 24

Gly Gly Gly Met Asn Ile Gln Met Leu Leu Glu Ala Ala Asp Tyr Leu
 1               5                  10                  15

Glu

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence:Synthetic
      peptide.

<400> SEQUENCE: 25

Gly Gly Gly Met Asn Ile Gln Met Pro Leu Glu Ala Pro Asp Tyr Leu
 1               5                  10                  15

Glu

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence:Synthetic
      peptide.

<400> SEQUENCE: 26

Gly Gly Gly Met Asn Ile Gln Met Leu Leu Glu Asp Ala Asp Tyr Leu
 1               5                  10                  15

Glu

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence:Synthetic
      peptide.

<400> SEQUENCE: 27

Gly Gly Gly Met Asn Ile Gln Met Leu Leu Glu Ala Ala Asp Tyr Asp
 1               5                  10                  15

Glu
```